(12) United States Patent
Monteleone et al.

(10) Patent No.: US 10,081,809 B2
(45) Date of Patent: Sep. 25, 2018

(54) METHODS OF TREATING DIABETES AND/OR PROMOTING SURVIVAL OF PANCREATIC ISLETS AFTER TRANSPLANTATION

(71) Applicants: Nogra Pharma Limited, Dublin 2 (IE); University of Miami, Miami, FL (US)

(72) Inventors: Giovanni Monteleone, Grottaferrata (IT); Peter Buchwald, Miami, FL (US); Luca Inverardi, Miami, FL (US); Antonello Pileggi, Miami, FL (US); Camillo Ricordi, Miami, FL (US); Alice Tomei, Miami, FL (US)

(73) Assignees: University of Miami, Miami, FL (US); Nogra Pharma Limited, Dublin 2 (IE)

( * ) Notice: Subject to any disclaimer, the term of this patent is extended or adjusted under 35 U.S.C. 154(b) by 0 days.

(21) Appl. No.: 14/394,999

(22) PCT Filed: Apr. 18, 2013

(86) PCT No.: PCT/US2013/037150
§ 371 (c)(1),
(2) Date: Oct. 16, 2014

(87) PCT Pub. No.: WO2013/158868
PCT Pub. Date: Oct. 24, 2013

(65) Prior Publication Data
US 2015/0315573 A1    Nov. 5, 2015

Related U.S. Application Data

(60) Provisional application No. 61/625,904, filed on Apr. 18, 2012.

(51) Int. Cl.
*C12N 15/113* (2010.01)
*A61K 9/00* (2006.01)

(52) U.S. Cl.
CPC .......... *C12N 15/113* (2013.01); *A61K 9/0019* (2013.01); *C12N 2310/11* (2013.01); *C12N 2310/3341* (2013.01); *C12N 2320/30* (2013.01)

(58) Field of Classification Search
CPC .................................................. C12N 15/113
See application file for complete search history.

(56) References Cited

U.S. PATENT DOCUMENTS

| | | | |
|---|---|---|---|
| 7,700,572 B2 | 4/2010 | Steinbrecher et al. | |
| 7,700,757 B2 | 4/2010 | Monteleone | |
| 7,807,818 B2 | 10/2010 | Monteleone | |
| 8,106,182 B2 | 1/2012 | Monteleone | |
| 8,648,186 B2 | 2/2014 | Monteleone | |
| 8,907,078 B2 | 12/2014 | Monteleone | |
| 8,912,154 B2 | 12/2014 | Baroni et al. | |
| 9,006,418 B2 | 4/2015 | Monteleone | |
| 9,096,854 B1 | 8/2015 | Monteleone | |
| 9,279,126 B2 | 3/2016 | Monteleone | |
| 9,314,434 B2 | 4/2016 | Baroni et al. | |
| 9,382,541 B2 | 7/2016 | Monteleone | |
| 9,499,819 B2 | 11/2016 | Baroni et al. | |
| 9,518,264 B2 | 12/2016 | Monteleone | |
| 9,605,264 B2 | 3/2017 | Monteleone | |
| 9,791,442 B2 | 10/2017 | Monteleone et al. | |
| 9,951,334 B2 | 4/2018 | Monteleone | |
| 2005/0119203 A1 | 6/2005 | Steinbrecher et al. | |
| 2007/0042985 A1 | 2/2007 | Monteleone | |
| 2007/0167385 A1 | 7/2007 | Monteleone | |
| 2009/0156539 A1 | 6/2009 | Monteleone | |
| 2010/0317719 A1 | 12/2010 | Monteleone | |
| 2011/0207795 A1 | 8/2011 | Steinbrecher et al. | |
| 2012/0015033 A1* | 1/2012 | Baroni ................ | C12N 15/113 424/482 |
| 2012/0136043 A1 | 5/2012 | Monteleone | |
| 2014/0142163 A1 | 5/2014 | Monteleone | |
| 2014/0256788 A1 | 9/2014 | Monteleone | |
| 2014/0271860 A1 | 9/2014 | Monteleone et al. | |
| 2015/0125523 A1 | 5/2015 | Baroni et al. | |
| 2015/0148245 A1 | 5/2015 | Monteleone et al. | |
| 2015/0211011 A1 | 7/2015 | Monteleone | |
| 2015/0218561 A1 | 8/2015 | Monteleone | |
| 2015/0232854 A1 | 8/2015 | Baroni et al. | |
| 2015/0337312 A1 | 11/2015 | Monteleone | |
| 2016/0177306 A1 | 6/2016 | Monteleone | |
| 2016/0222383 A1 | 8/2016 | Baroni et al. | |
| 2016/0304876 A1 | 10/2016 | Monteleone | |
| 2017/0107520 A1 | 4/2017 | Baroni et al. | |
| 2017/0233736 A1 | 8/2017 | Monteleone et al. | |
| 2017/0240893 A1 | 8/2017 | Monteleone | |
| 2017/0253880 A1 | 9/2017 | Monteleone | |
| 2018/0030450 A1 | 2/2018 | Monteleone | |

FOREIGN PATENT DOCUMENTS

| | | | |
|---|---|---|---|
| WO | WO-2002/010214 A2 | | 2/2002 |
| WO | WO 03/037368 | * | 5/2003 |
| WO | WO-2004/087920 A1 | | 10/2004 |
| WO | WO2004087920 A1 | * | 10/2004 |
| WO | WO-2005/014782 A2 | | 2/2005 |

(Continued)

OTHER PUBLICATIONS

Rejman et al. Nucleosides, Nucleotides & Nucleic Acids, 20, 819-823, 2001.*
Jooset et al. Methods in Molecular Biology Human Press 933 Springer Protocols Animal Models in Diabetes Research, pp. 1-321, 2012.*

(Continued)

*Primary Examiner* — Brian A Whiteman
(74) *Attorney, Agent, or Firm* — Goodwin Procter LLP

(57) ABSTRACT

Disclosed herein are methods for treating/and or preventing diabetes using a specific inhibitor of SMAD7 expression or function. Also disclosed are methods of promoting organ and/or cell, e.g., pancreatic islet cell, survival after transplantation using a specific inhibitor of SMAD7 expression or function.

26 Claims, 12 Drawing Sheets
(2 of 12 Drawing Sheet(s) Filed in Color)
Specification includes a Sequence Listing.

(56) References Cited

FOREIGN PATENT DOCUMENTS

| | | |
|---|---|---|
| WO | WO-2005/050202 A2 | 6/2005 |
| WO | WO-2006-035434 A2 | 4/2006 |
| WO | WO-2007/039151 A1 | 4/2007 |
| WO | WO-2009/129544 A1 | 10/2009 |
| WO | WO-2010/054826 A1 | 5/2010 |
| WO | WO-2013/037970 A1 | 3/2013 |
| WO | WO-2014/140333 A1 | 9/2014 |
| WO | WO-2015/169966 A2 | 11/2015 |
| WO | WO-2016/059239 A1 | 4/2016 |
| WO | WO-2016/059243 A2 | 4/2016 |
| WO | WO-2017/055611 A2 | 4/2017 |
| WO | WO-2017/144689 A1 | 8/2017 |

OTHER PUBLICATIONS

Badaru A and Pihoker C, (2012) 'Type 2 Diabetes in Childhood: Clinical Characteristics and Role of β-Cell Autoimmunity,' Curr Diab Rep, 12(1):75-81.

Bhat BG et al., (2007) 'Antisense Inhibition of 11betahydroxysteroid Dehydrogenase Type 1 Improves Diabetes in a Novel Cortisone-Induced Diabetic KK Mouse Model,' Biochem Biophys Res Commun, 365(4):740-5.

Chen HY et al., (2010) 'The Protective Role of Smad7 in Diabetic Kidney Disease: Mechanism and Therapeutic Potential,' Diabetes, 60(2):590-601.

Gutierrez-Aguilar R et al., (2007) 'Minor Contribution of SMAD7 and KLF10 Variants to Genetic Susceptibility of Type 2 Diabetes,' Diabetes Metab, 33(5):372-8.

Hong S et al., (2007) 'Smad7 Sensitizes Tumor Necrosis Factor Induced Apoptosis Through the Inhibition of Antiapoptotic Gene Expression by Suppressing Activation of the Nuclear Factor-κβ Pathway,' Cancer Res, 67(19):9577-83.

Hook SM et al., (2011) 'Smad2: A Candidate Gene for the Murine Autoimmune Diabetes Locus Idd21.1,' J Clin Endocrinol Metab, 96(12):E2072-7.

International Search Report for PCT/US2013/037150, dated Jul. 29, 2013 (6 pages).

Kawamoto K et al., (2010) 'Transforming Growth Factor β-1 (TGF-β-1) and Rapamycin Synergize to Effectively Suppress Human T Cell Responses via Upregulation of FoxP3+ Tregs,' Transpl Immunol, 23(1-2):28-33.

Li MO and Flavell RA, (2008) 'TGF-β: A Master of all T Cell Trades,' Cell, 134(3):392-404.

Liang Y et al., (2004) 'Reduction in Glucagon Receptor Expression by an Antisense Oligonucleotide Ameliorates Diabetic Syndrome in db/db Mice,' Diabetes, 53(2):410-17.

Luo X et al., (2005) 'Systemic Transforming Growth Factor-β1 Gene Therapy Induces Foxp3+ Regulatory Cells, Restores Self-Tolerance, and Facilitates Regeneration of β-Cell Function in Overtly Diabetic Nonobese Diabetic Mice,' Transplantation, 79(9):1091-6.

Margolles-Clark E et al., (2009) 'Small-Molecule Costimulatory Blockade: Organic Dye Inhibitors of the CD40-CD154 Interaction,' J Mol Med, 87(11):1133-43.

Mizobuchi T et al., (2003) 'Differential Expression of Smad7 Transcripts Identifies the CD4+CD45RChigh Regulatory T Cells that Mediate Type V Collagen-Induced Tolerance to Lung Allografts,' J Immunol, 171(3):1140-7.

Monteleone G et al., (2004) 'A Failure of Transforming Growth Factor-β-1 Negative Regulation Maintains sustained NF-κβ Activation in Gut Inflammation,' J Biol Chem, 279(6):3925-32.

Moritani M et al., (1998) 'Abrogation of Autoimmune Diabetes in Nonobese Diabetic Mice and Protection Against Effector Lymphocytes by Transgenic Paracrine TGF-β1,' J Clin Invest, 102(3):499-506.

Olivieri A et al., (2010) 'Serum Transforming Growth Factor β1 During Diabetes Development in Non-Obese Diabetic Mice and Humans,' Clin Exp Immunol, 162(3):407-14.

Roep BO et al., (2004) 'Satisfaction (not) Guaranteed: Re-Evaluating the Use of Animal Models of Type 1 Diabetes,' Nat Rev Immunol, 4(12):989-97.

Shoda LK et al., (2005) 'A Comprehensive Review of Interventions in the NOD Mouse and Implications for Translation,' Immunity, 23(2):115-26.

Smart NG et al., (2006) 'Conditional Expression of Smad7 in Pancreatic β Cells Disrupts TGF-β Signaling and Induces Reversible Diabetes Mellitus,' PLoS Biol. 4(2):e39. p. 200-209.

Written Opinion of the International Searching Authority for PCT/US2013/037150, dated Jul. 29, 2013 (5 pages).

Wållberg M et al., (2011) 'An Islet-Specific Pulse of TGF-β Abrogates CTL Function and Promotes β Cell Survival Independent of Foxp3+ T Cells,' J Immunol, 186(4):2543-51.

Yan X and Chen YG, (2011) 'Smad7: Not Only a Regulator, but also a Cross-Talk Mediator of TGF-β Signalling,' Biochem J, 434:1-10.

Zhu L et al., (2011) 'Unraveling the Biological Functions of Smad7 with Mouse Models,' Cell Biosci, 1(44):1-6.

Akhurst RJ and Hata A, (2012), 'Targeting the TGFβ Signalling Pathway in Disease,' Nat Rev Drug Discov, 11(10):790-811.

Alanentalo T et al., (2010), 'Quantification and Three-Dimensional Imaging of the Insulitis-Induced Destruction of β-Cells in Murine Type 1 Diabetes,' Diabetes, 59(7):1756-64.

Anderson MS and Bluestone JA, (2005), 'The NOD Mouse: A Model of Immune Dysregulation,' Annu Rev Immunol, 23:447-85.

Ardizzone S et al., (2016), 'Mongersen, an Oral Smad7 Antisense Oligonucleotide, in Patients with Active Crohn's Disease,' Therap Adv Gastroenterol, 9(4):527-32.

Atkinson MA et al., (2014), 'Type 1 Diabetes,' Lancet, 383(9911):69-82 (NIH Public Access Author Manuscript).

Chong AS et al., (2006), 'Reversal of Diabetes in Non-Obese Diabetic Mice without Spleen Cell-Derived β Cell Regeneration,' Science, 311(5768):1774-5.

Diabetes.co.uk (2017), 'Differences Between Type 1 and Type 2 Diabetes,' downloaded from the internet on Feb. 27, 2017 from <<http://www.diabetes.co.uk/difference-between-type1-and-type2-diabetes.html> (3 pages).

Donath MY and Shoelson SE, (2011), 'Type 2 Diabetes as an Inflammatory Disease,' Nat Rev Immunol, 11(2):98-107.

Donath MY, (2014), 'Targeting Inflammation in the Treatment of Type 2 Diabetes: Time to Start,' Nat Rev Drug Discov, 13(6):465-76.

Fantini MC et al., (2004), 'Cutting Edge: TGF-β Induces a Regulatory Phenotype in CD4$^+$CD25 T Cells Through Foxp3 Induction and Down-Regulation of Smad7,' J Immunol, 172(9):5149-53.

Letterio JJ and Roberts AB, (1998), 'Regulation of Immune Responses by TGF-β,' Annu Rev Immunol, 16:137-61.

Liston A et al., (2017), 'Beta-Cell Fragility as a Common Underlying Risk Factor in Type 1 and Type 2 Diabetes,' Trends Mol Med, 23(2):181-94.

Mangan PR et al., (2006), 'Transforming Growth Factor-β Induces Development of the T(H)17 Lineage,' Nature, 441(7090):231-4.

Matveyenko AV and Butler PC, (2008), 'Relationship Between β-Cell Mass and Diabetes Onset,' Diabetes Obes Metab, 10(Suppl 4):23-31.

Monteleone G et al., (2001), 'Blocking Smad7 Restores TGF-β1 Signaling in Chronic Inflammatory Bowel Disease,' J Clin Invest, 108(4):601-9.

Nir T et al., (2007), 'Recovery from Diabetes in Mice by β Cell Regeneration,' J Clin Invest, 117(9):2553-61.

Penfornis A and Kury-Paulin S, (2006), 'Immunosuppressive Drug-Induced Diabetes,' Diabetes Metab, 32(5 Pt 2):539-46.

Reed JC and Herold KC, (2015), 'Thinking Bedside at the Bench: The NOD Mouse Model of T1DM,' Nat Rev Endocrinol, 11(5):308-14 (NIH Public Access Author Manuscript).

Sherry NA et al., (2007), 'Exendin-4 Improves Reversal of Diabetes in NOD Mice Treated with Anti-CD3 Monoclonal Antibody by Enhancing Recovery of β-Cells,' Endocrinology, 148(11):5136-44.

Skyler JS and Ricordi C, (2011), 'Stopping Type 1 Diabetes: Attempts to Prevent of Cure Type 1 Diabetes in Man,' Diabetes, 60(1):1-8.

(56) References Cited

OTHER PUBLICATIONS

Skyler JS, (2015), 'Prevention and Reversal of Type 1 Diabetes—Past Challenges and Future Opportunities,' Diabetes Care, 38(6):997-1007.
Wilkinson A et al., (2005), 'Guidelines for the Treatment and Management of New-Onset Diabetes After Transplantation,' Clin Transplant, 19(3):291-8.
Zahr E et al., (2007), 'Rapamycin Impairs in vivo Proliferation of Islet β-Cells,' Transplantation, 84(12):1576-83.
Piccirillo CA et al., (1998), 'TGF-β1 Somatic Gene Therapy Prevents Autoimmune Disease in Nonobese Diabetic Mice,' J Immunol, 161(8):3950-6.

* cited by examiner

FIG. 1A

```
   1 ggcacgagcg gagagccgcg cagggcgcgg gccgcgcggg gtggggcagc cggagcgcag
  61 gcccccgatc cccggcgggc gcccccgggc ccccgcgcgc gccccggcct ccgggagact
 121 ggcgcatgcc acggagcgcc cctcgggccg ccgccgctcc tgcccgggcc cctgctgctg
 181 ctgctgtcgc ctgcgcctgc tgccccaact cggcgcccga cttcttcatg gtgtgcggag
 241 gtcatgttcg ctccttagca ggcaaacgac ttttctcctc gcctcctcgc cccgcatgtt
 301 caggaccaaa cgatctgcgc tcgtccggcg tctctggagg agccgtgcgc ccggcggcga
 361 ggacgaggag gagggcgcag ggggaggtgg aggaggaggc gagctgcggg gagaaggggc
 421 gacggacagc cgagcgcatg gggccggtgg cggcggcccg ggcagggctg gatgctgcct
 481 gggcaaggcg gtgcgaggtg ccaaaggtca ccaccatccc cacccgccag ccgcgggcgc
 541 cggcgcggcc gggggcgccg aggcggatct gaaggcgctc acgcactcgg tgctcaagaa
 601 actgaaggag cggcagctgg agctgctgct ccaggccgtg gagtcccgcg gcgggacgcg
 661 caccgcgtgc ctcctgctgc ccggccgcct ggactgcagg ctgggcccgg gggcgcccgc
 721 cggcgcgcag cctgcgcagc cgccctcgtc ctactcgctc cccctcctgc tgtgcaaagt
 781 gttcaggtgg ccggatctca ggcattcctc ggaagtcaag aggctgtgtt gctgtgaatc
 841 ttacgggaag atcaacccccg agctggtgtg ctgcaacccc catcacctta gccgactctg
 901 cgaactagag tctccccccc ctccttactc cagatacccg atggattttc tcaaaccaac
 961 tgcagactgt ccagatgctg tgccttcctc cgctgaaaca gggggaacga attatctggc
1021 ccctggggggg ctttcagatt cccaacttct tctggagcct ggggatcggt cacactggtg
1081 cgtggtggca tactgggagg agaagacgag agtggggagg ctctactgtg tccaggagcc
1141 ctctctggat atcttctatg atctacctca ggggaatggc ttttgcctcg gacagctcaa
1201 ttcggacaac aagagtcagc tggtgcagaa ggtgcggagc aaaatcggct gcggcatcca
1261 gctgacgcgg gaggtggatg gtgtgtgggt gtacaaccgc agcagttacc ccatcttcat
1321 caagtccgcc acactggaca acccggactc caggacgctg ttggtacaca aggtgttccc
1381 cggtttctct atcaaggctt tcgactacga gaaggcgtac agcctgcagc ggcccaatga
1441 ccacgagttt atgcagcagc cgtggacggg ctttaccgtg cagatcagct ttgtgaaggg
1501 ctggggtcag tgctacaccc gccagttcat cagcagctgc ccgtgctggc tagaggtcat
1561 cttcaacagc cggtagccgc gtgcggaggg gacagagcgt gagctgagca ggccacactt
1621 caaactactt tgctgctaat atttttcctcc tgagtgcttg cttttcatgc aaactctttg
1681 gtcgtttttt ttttgtttgt tggttggttt tcttcttctc gtcctcgttt gtgttctgtt
1741 ttgtttcgct ctttgagaaa tagcttatga aaagaattgt tgggggtttt tttggaagaa
1801 ggggcaggta tgatcggcag gacaccctga taggaagagg ggaagcagaa atccaagcac
1861 caccaaacac agtgtatgaa ggggggcggt catcatttca cttgtcagga gtgtgtgtga
1921 gtgtgagtgt gcggctgtgt gtgcacgcgt gtgcaggagc ggcagatggg gagacaacgt
1981 gctcttttgtt ttgtgtctct tatggatgtc cccagcagag aggtttgcag tcccaagcgg
2041 tgtctctcct gccccttgga cacgctcagt ggggcagagg cagtcctggg gcaagctggc
2101 ggctggggtc ccagcagctg ccaggagcac ggctctgtcc ccagcctggg aaagccctg
2161 cccctcctct ccctcatcaa ggacacgggc ctgtccacag gcttctgagc agcgagcctg
2221 ctagtggccg aaccagaacc aattattttc atccttgtct tattcccttc ctgccagccc
2281 ctgccattgt agcgtctttc ttttttggcc atctgctcct ggatctccct gagatgggct
2341 tccaagggc tgccggggca gcccctcac agtattgctc acccagtgcc ctctcccctc
2401 agcctctccc ctgcctgccc tggtgacatc aggttttcc cggacttaga aaaccagctc
2461 agcactgcct gctcccatcc tgtgtgttaa gctctgctat taggccagca agcggggatg
2521 tccctgggag ggacatgctt agcagtcccc ttccctccaa gaaggatttg gtccgtcata
2581 acccaaggta ccatcctagg ctgacaccta actcttcttt catttcttct acaactcata
2641 cactcgtatg atacttcgac actgttctta gctcaatgag catgtttaga ctttaacata
2701 agctatttt ctaactacaa aggtttaaat gaacaagaga agcattctca ttggaaattt
2761 agcattgtag tgctttgaga gagaaggac tcctgaaaaa aaacctgaga tttattaaag
2821 aaaaaaatgt attttatgtt atatataaat atattattac ttgtaaatat aaagacgttt
2881 tataagcatc attatttatg tattgtgcaa tgtgtataaa caagaaaaat aaagaaaaga
2941 tgcactttgc tttaatataa atgcaaataa caaatgccaa attaaaaaag ataaacacaa
3001 gattggtgtt ttttcctatg ggtgttatca cctagctgaa tgttttttcta aaggagttta
3061 tgttccatta aacgattttt aaaatgtaca cttgaaaaaa aaaaaaaaaa a
(SEQ ID NO: 1)
```

FIG. 1B

```
MERTKRSALVRRLWRSRAPGGEDEEEGAGGGGGGGELRGEGATD
SRAHGAGGGGPGRAGCCLGKAVRGAKGHHHPHPPAAGAGAAGGAEADLKALTHSVLKK
LKERQLELLLQAVESRGGTRTACLLLPGRLDCRLGPGAPAGAQPAQPPSSYSLPLLLC
KVFRWPDLRHSSEVKRLCCCESYGKINPELVCCNPHHLSRLCELESPPPPYSRYPMDF
LKPTADCPDAVPSSAETGGTNYLAPGGLSDSQLLLEPGDRSHWCVVAYWEEKTRVGRL
YCVQEPSLDIFYDLPQGNGFCLGQLNSDNKSQLVQKVRSKIGCGIQLTREVDGVWVYN
RSSYPIFIKSATLDNFDSRTLLVHKVFPGFSIKAFDYEKAYSLQRPNDHEFMQQPWTG
FTVQISFVKGWGQCYTRQFISSCPCWLEVIFNSR
(SEQ ID NO:2)
```

GED-0301 Intervention Study in Hyperglycemic NOD Mice, Representative
Pancreas Sections Stained for Insulin and Glucagon

SEQUENCE LISTING

```
<160> NUMBER OF SEQ ID NOS: 12

<210> SEQ ID NO 1
<211> LENGTH: 3111
<212> TYPE: DNA
<213> ORGANISM: Homo sapiens

<400> SEQUENCE: 1
ggcacgagcg gagagccgcg cagggcgcgg gccgcgcggg gtggggcagc cggagcgcag      60
gcccccgatc cccggcgggc gccccgggc ccccgcgcgc gccccggcct ccgggagact     120
ggcgcatgcc acggagcgcc cctcgggccg ccgccgctcc tgcccgggcc cctgctgctg     180
ctgctgtcgc ctgcgcctgc tgccccaact cggcgcccga cttcttcatg gtgtgcggag     240
gtcatgttcg ctccttagca ggcaaacgac ttttctcctc gcctcctcgc cccgcatgtt     300
caggaccaaa cgatctgcgc tcgtccggcg tctctggagg agccgtgcgc ccggcggcga     360
ggacgaggag gagggcgcag ggggaggtgg aggaggaggc gagctgcggg gagaagggc      420
```

-continued

```
gacggacagc cgagcgcatg gggccggtgg cggcggcccg gcagggctg gatgctgcct      480 gggcaaggcg gtgcgaggtg ccaaaggtca ccaccatccc cacccgccag ccgcgggcgc      540
cggcgcggcc gggggcgccg aggcggatct gaaggcgctc acgcactcgg tgctcaagaa      600
actgaaggag cggcagctgg agctgctgct ccaggccgtg gagtcccgcg gcggacgcg      660 caccgcgtgc ctcctgctgc ccggccgcct ggactgcagg ctgggcccgg ggcgcccgc      720 cggcgcgcag cctgcgcagc cgccctcgtc ctactcgctc ccctcctgc tgtgcaaagt      780 gttcaggtgg ccggatctca ggcattcctc ggaagtcaag aggctgtgtt gctgtgaatc      840
ttacgggaag atcaacccg agctggtgtg ctgcaacccc catcacctta gccgactctg      900
cgaactagag tctcccccc ctccttactc cagatacccg atggattttc tcaaaccaac      960
tgcagactgt ccagatgctg tgccttcctc cgctgaaaca gggggaacga attatctggc     1020
ccctgggggg ctttcagatt cccaacttct tctggagcct ggggatcggt cacactggtg     1080
cgtggtggca tactgggagg agaagacgag agtggggagg ctctactgtg tccaggagcc     1140
ctctctggat atcttctatg atctacctca ggggaatggc ttttgcctcg acagctcaa      1200 ttcggacaac aagagtcagc tggtgcagaa ggtgcggagc aaaatcggct gcggcatcca     1260
gctgacgcgg gaggtggatg gtgtgtgggt gtacaaccgc agcagttacc ccatcttcat     1320
caagtccgcc acactggaca acccggactc caggacgctg ttggtacaca aggtgttccc     1380
cggtttctcc atcaaggctt tcgactacga aaggcgtac agcctgcagc ggcccaatga     1440
ccacgagttt atgcagcagc cgtggacggg ctttaccgtg cagatcagct ttgtgaaggg     1500
ctggggtcag tgctacaccc gccagttcat cagcagctgc ccgtgctggc tagaggtcat     1560
cttcaacagc cggtagccgc gtgcggaggg gacagagcgt gagctgagca ggccacactt     1620
caaactactt tgctgctaat attttcctcc tgagtgcttg cttttcatgc aaactctttg     1680 gtcgttttt tttgtttgt tggttggttt tcttcttctc gtcctcgttt gtgttctgtt     1740
ttgtttcgct ctttgagaaa tagcttatga aaagaattgt tggggtttt tttgaagaa      1800 ggggcaggta tgatcggcag gacaccctga taggaagagg ggaagcagaa atccaagcac     1860
caccaaacac agtgtatgaa ggggggcggt catcatttca cttgtcagga gtgtgtgtga     1920
gtgtgagtgt gcggctgtgt gtgcacgcgt gtgcaggagc ggcagatggg gagacaacgt     1980
gctctttgtt ttgtgtctct tatggatgtc cccagcagag aggtttgcag tcccaagcgg     2040
tgtctctcct gccccttgga cacgctcagt ggggcagagg cagtacctgg gcaagctggc     2100
ggctggggtc ccagcagctg ccaggagcac ggctctgtcc ccagcctggg aaagcccctg     2160
cccctcctct ccctcatcaa ggacacgggc ctgtccacag gcttctgagc agcgagcctg     2220
ctagtggccg aaccagaacc aattattttc atccttgtct tattcccttc ctgccagccc     2280
ctgccattgt agcgtctttc tttttttggcc atctgctcct ggatctccct gagatgggct     2340
tcccaagggc tgccggggca gccccctcac agtattgctc acccagtgcc ctctcccctc     2400
agcctctccc ctgcctgccc tggtgacatc aggttttttcc cggacttaga aaaccagctc     2460
agcactgcct gctcccatcc tgtgtgttaa gctctgctat taggccagca agcggggatg     2520
tccctgggag ggacatgctt agcagtcccc ttccctccaa gaaggatttg gtccgtcata     2580
acccaaggta ccatcctagg ctgacaccta actcttcttt catttcttct acaactcata     2640
cactcgtatg atacttcgac actgttctta gctcaatgag catgtttaga ctttaacata     2700 agctatttt ctaactacaa aggtttaaat gaacaagaga agcattctca ttggaaattt     2760
agcattgtag tgctttgaga gagaaaggac tcctgaaaaa aaacctgaga tttattaaag     2820
```

-continued

```
aaaaaaatgt attttatgtt atatataaat atattattac ttgtaaatat aaagacgttt    2880
tataagcatc attatttatg tattgtgcaa tgtgtataaa caagaaaaat aaagaaaaga    2940
tgcactttgc tttaatataa atgcaaataa caaatgccaa attaaaaaag ataaacacaa    3000
gattggtgtt ttttcctatg ggtgttatca cctagctgaa tgttttttcta aaggagttta   3060 tgttccatta aacgattttt aaaatgtaca cttgaaaaaa aaaaaaaaa a              3111
```

<210> SEQ ID NO 2
<211> LENGTH: 425
<212> TYPE: PRT
<213> ORGANISM: Homo sapiens

<400> SEQUENCE: 2

```
Met Phe Arg Thr Lys Arg Ser Ala Leu Val Arg Arg Leu Trp Arg Ser
1               5                   10                  15

Arg Ala Pro Gly Gly Glu Asp Glu Glu Gly Ala Gly Gly Gly Gly Gly
            20                  25                  30

Gly Gly Gly Glu Leu Arg Gly Gly Ala Thr Asp Ser Arg Ala His
        35                  40                  45

Gly Ala Gly Gly Gly Pro Gly Arg Ala Gly Cys Cys Leu Gly Lys
    50                  55                  60

Ala Val Arg Gly Ala Lys Gly His His His Pro His Pro Pro Ala Ala
65                  70                  75                  80

Gly Ala Gly Ala Ala Gly Gly Ala Glu Ala Asp Leu Lys Ala Leu Thr
                85                  90                  95

His Ser Val Leu Lys Lys Leu Lys Glu Arg Gln Leu Glu Leu Leu
            100                 105                 110

Gln Ala Val Glu Ser Arg Gly Gly Thr Arg Thr Ala Cys Leu Leu Leu
        115                 120                 125

Pro Gly Arg Leu Asp Cys Arg Leu Gly Pro Gly Ala Pro Ala Gly Ala
    130                 135                 140

Gln Pro Ala Gln Pro Pro Ser Ser Tyr Ser Leu Pro Leu Leu Leu Cys
145                 150                 155                 160

Lys Val Phe Arg Trp Pro Asp Leu Arg His Ser Ser Glu Val Lys Arg
                165                 170                 175

Leu Cys Cys Cys Glu Ser Tyr Gly Lys Ile Asn Pro Glu Leu Val Cys
            180                 185                 190

Cys Asn Pro His His Leu Ser Arg Leu Cys Glu Leu Glu Ser Pro Pro
        195                 200                 205

Pro Pro Tyr Ser Arg Tyr Pro Met Asp Phe Leu Lys Pro Thr Ala Asp
    210                 215                 220

Cys Pro Asp Ala Val Pro Ser Ser Ala Glu Thr Gly Gly Thr Asn Tyr
225                 230                 235                 240

Leu Ala Pro Gly Gly Leu Ser Asp Ser Gln Leu Leu Leu Glu Pro Gly
                245                 250                 255

Asp Arg Ser His Trp Cys Val Val Ala Tyr Trp Glu Glu Lys Thr Arg
            260                 265                 270

Val Gly Arg Leu Tyr Cys Val Gln Glu Pro Ser Leu Asp Ile Phe Tyr
        275                 280                 285

Asp Leu Pro Gln Gly Asn Gly Phe Cys Leu Gly Gln Leu Asn Ser Asp
    290                 295                 300

Asn Lys Ser Gln Leu Val Gln Lys Val Arg Ser Lys Ile Gly Cys Gly
305                 310                 315                 320
```

```
Ile Gln Leu Thr Arg Glu Val Asp Gly Val Trp Val Tyr Asn Arg Ser
            325                 330                 335

Ser Tyr Pro Ile Phe Ile Lys Ser Ala Thr Leu Asp Asn Pro Asp Ser
            340                 345                 350

Arg Thr Leu Leu Val His Lys Val Phe Pro Gly Phe Ser Ile Lys Ala
            355                 360                 365

Phe Asp Tyr Glu Lys Ala Tyr Ser Leu Gln Arg Pro Asn Asp His Glu
            370                 375                 380

Phe Met Gln Gln Pro Trp Thr Gly Thr Val Gln Ile Ser Phe Val Lys
385                 390                 395                 400

Gly Trp Gly Gln Cys Tyr Thr Arg Gln Phe Ile Ser Ser Cys Pro Cys
            405                 410                 415

Trp Leu Glu Val Ile Phe Asn Ser Arg
            420                 425

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtcgcccctt ctccccgcag c                                              21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: Cytosine, 5-methylcytosine or
      2'-O-methylcytosine
<220> FEATURE:
<221> NAME/KEY: modified_base
<222> LOCATION: (4)..(4)
<223> OTHER INFORMATION: Guanine, 5-methylguanine or 2'-O-methylguanine
<220> FEATURE:
<221> NAME/KEY: modified_base
<222> LOCATION: (16)..(16)
<223> OTHER INFORMATION: Cytosine, 5-methylcytosine or
      2'-O-methylcytosine
<220> FEATURE:
<221> NAME/KEY: modified_base
<222> LOCATION: (17)..(17)
<223> OTHER INFORMATION: Guanine, 5-methylguanine or 2'-O-methylguanine

<400> SEQUENCE: 4
gtcgcccctt ctccccgcag                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-methyl 2'-deoxycytidine 5'-monophosphate
```

-continued

```
<220> FEATURE:
<221> NAME/KEY: modified_base
<222> LOCATION: (16)..(16)
<223> OTHER INFORMATION: 5-methyl 2'-deoxycytidine 5'-monophosphate

<400> SEQUENCE: 5
gtcgcccctt ctccccgcag                                                   20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-methyl 2'-deoxycytidine 5'-monophosphate
<220> FEATURE:
<221> NAME/KEY: modified_base
<222> LOCATION: (16)..(16)
<223> OTHER INFORMATION: 5-methyl 2'-deoxycytidine 5'-monophosphate

<400> SEQUENCE: 6
gtcgcccctt ctccccgcag c                                                 21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxyguanosine methylphosphonate
<220> FEATURE:
<221> NAME/KEY: modified_base
<222> LOCATION: (3)..(3)
<223> OTHER INFORMATION: 5-methyl 2'-deoxycytidine 5'-monophosphate
<220> FEATURE:
<221> NAME/KEY: modified_base
<222> LOCATION: (16)..(16)
<223> OTHER INFORMATION: 5-methyl 2'-deoxycytidine 5'-monophosphate
<220> FEATURE:
<221> NAME/KEY: modified_base
<222> LOCATION: (20)..(20)
<223> OTHER INFORMATION: 2'-deoxyguanosine methylphosphonate

<400> SEQUENCE: 7
gtcgcccctt ctccccgcag                                                   20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxyguanosine methylphosphonate
<220> FEATURE:
<221> NAME/KEY: modified_base
<222> LOCATION: (3)..(3)
<223> OTHER INFORMATION: 5-methyl 2'-deoxycytidine 5'-monophosphate
<220> FEATURE:
<221> NAME/KEY: modified_base
<222> LOCATION: (16)..(16)
<223> OTHER INFORMATION: 5-methyl 2'-deoxycytidine 5'-monophosphate
```

-continued

```
<220> FEATURE:
<221> NAME/KEY: modified_base
<222> LOCATION: (20)..(20)
<223> OTHER INFORMATION: 2'-deoxyguanosine methylphosphonate

<400> SEQUENCE: 8
gtcgcccctt ctccccgcag c                                              21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-methyl 2'-deoxycytidine
      5'-monophosphorothioate
<220> FEATURE:
<221> NAME/KEY: modified_base
<222> LOCATION: (16)..(16)
<223> OTHER INFORMATION: 5-methyl 2'-deoxycytidine
      5'-monophosphorothioate

<400> SEQUENCE: 9
gtcgcccctt ctccccgcag                                                20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-methyl 2'-deoxycytidine
      5'-monophosphorothioate
<220> FEATURE:
<221> NAME/KEY: modified_base
<222> LOCATION: (16)..(16)
<223> OTHER INFORMATION: 5-methyl 2'-deoxycytidine
      5'-monophosphorothioate

<400> SEQUENCE: 10
gtcgcccctt ctccccgcag c                                              21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxyguanosine methylthiophosphonate
<220> FEATURE:
<221> NAME/KEY: modified_base
<222> LOCATION: (3)..(3)
<223> OTHER INFORMATION: 5-methyl 2'-deoxycytidine 5'-monophosphate
<220> FEATURE:
<221> NAME/KEY: modified_base
<222> LOCATION: (16)..(16)
<223> OTHER INFORMATION: 5-methyl 2'-deoxycytidine 5'-monophosphate
<220> FEATURE:
<221> NAME/KEY: modified_base
<222> LOCATION: (20)..(20)
<223> OTHER INFORMATION: 2'-deoxyguanosine methylthiophosphonate
```

```
<400> SEQUENCE: 11
gtcgcccctt ctccccgcag                                                    20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxyguanosine methylthiophosphonate
<220> FEATURE:
<221> NAME/KEY: modified_base
<222> LOCATION: (3)..(3)
<223> OTHER INFORMATION: 5-methyl 2'-deoxycytidine 5'-monophosphate
<220> FEATURE:
<221> NAME/KEY: modified_base
<222> LOCATION: (16)..(16)
<223> OTHER INFORMATION: 5-methyl 2'-deoxycytidine 5'-monophosphate
<220> FEATURE:
<221> NAME/KEY: modified_base
<222> LOCATION: (20)..(20)
<223> OTHER INFORMATION: 2'-deoxyguanosine methylthiophosphonate

<400> SEQUENCE: 12
gtcgcccctt ctccccgcag c                                                  21
```

METHODS OF TREATING DIABETES AND/OR PROMOTING SURVIVAL OF PANCREATIC ISLETS AFTER TRANSPLANTATION

CROSS REFERENCE TO RELATED APPLICATION

This application is the U.S. national stage of International (PCT) Patent Application No. PCT/US2013/037150, filed Apr. 18, 2013, which claims priority to and the benefit of U.S. provisional application 61/625,904, filed Apr. 18, 2012, the entire contents of which are herein incorporated by reference.

FIELD OF THE INVENTION

The present invention is generally directed to antisense oligonucleotides against SMAD7 and uses thereof in treating and/or preventing diabetes and/or in promoting pancreatic islet cell survival after transplantation.

BACKGROUND

Diabetes is a metabolic disease characterized by high levels of sugar in the blood. The two most prevalent types of diabetes are Type 1 diabetes mellitus (T1DM) and Type 2 diabetes mellitus (T2DM). Type 1, or insulin-dependent diabetes mellitus (IDDM), is a chronic autoimmune disease characterized by the extensive loss of beta cells in the pancreatic islets, which produce insulin. Type 2 diabetes, or non-insulin dependent diabetes mellitus (NIDDM), develops when muscle, fat and liver cells fail to respond normally to insulin (insulin resistance). In particular, Type 2 diabetes has become an epidemic, driven by increases in obesity and a sedentary lifestyle, and the general aging of the populations in many countries. In recent clinical practice, it has become increasingly difficult to distinguish T1DM from T2DM as many children with T1DM are overweight at diagnosis, and a considerable proportion of physician-diagnosed T2DM youth have evidence of pancreatic autoimmunity (Badaru, A. and Pihoker, C. "Type 2 diabetes in childhood: clinical characteristics and role of beta-cell autoimmunity," *Curr. Diab. Rep.*, 2012, 12, 75-81). In 2011, more than 346 million people worldwide were affected by diabetes.

Recent studies have demonstrated that TGF-β plays a role in pancreatic islet function and diabetes development (Moritani, M. et al. "Abrogation of autoimmune diabetes in nonobese diabetic mice and protection against effector lymphocytes by transgenic paracrine TGF-β1," *J. Clin. Invest.*, 1998, 102, 499-506; Olivieri, A. et al. "Serum transforming growth factor β1 during diabetes development in non-obese diabetic mice and humans," *Clin. Exp. Immunol.*, 2010, 162, 407-414). For example, an islet-specific pulse of TGF-β expression for one week has been shown to delay diabetes development in NOD mice (Wållberg, M. et al. "An islet-specific pulse of TGF-β abrogates CTL function and promotes β cell survival independent of Foxp3+ T cells," *J. Immunol.*, 2011, 186, 2543-2551), a commonly used animal model of type 1 diabetes (Roep, B. O. et al. "Satisfaction (not) guaranteed: re-evaluating the use of animal models of type 1 diabetes," *Nat. Rev. Immunol.*, 2004, 4, 989-997). TGF-β1 was effective not only in curing diabetes in diabetic NOD mice and blocking islet destructive autoimmunity, but also in inducing islet regeneration (Luo, X. et al. "Systemic transforming growth factor-β gene therapy induces Foxp3+ regulatory cells, restores self-tolerance, and facilitates regeneration of beta cell function in overtly diabetic non-obese diabetic mice," *Transplantation*, 2005, 79, 1091-1096). Hence, therapeutic interventions along this pathway, may not only stop the progression of the disease, but might even restore function (i.e., adequate insulin production) after onset of hyperglycemia.

The TGF-βs 1-3 are involved in a variety of biological functions including cell growth, organ development, fibrogenesis, and regulation of immune cells. TGF-β1 is the predominant form expressed in the immune system, and it is now well-recognized as a critical regulator in immune responses that can dampen T cell responses (Li, M. O. and Flavell, R. A. "TGF-beta: a master of all T cell trades," *Cell*, 2008, 134, 392-404). Specifically, TGF-β1 binds a heterodimeric transmembrane serine/threonine kinase receptor containing two subunits, TGF-β1 R1 and TGF-β1 R2. Upon ligand binding, the TGF-β1 R1 receptor is phosphorylated by the constitutively active TGF-β1 R2 receptor and signal is propagated to the nucleus by proteins belonging to the SMAD family. Activated TGF-β1 R1 directly phosphorylates SMAD2 and SMAD3 proteins, which then interact with SMAD4. The complex of SMAD2/SMAD3/SMAD4 translocates to the nucleus and modulates the transcription of certain genes. SMAD7 is another member of this protein family that acts as a general antagonist for TGF-β through negative-feedback mechanisms (Yan, X. and Chen, Y. G. "Smad7: not only a regulator, but also a cross-talk mediator of TGF-beta signalling," *Biochem. J.*, 2011, 434, 1-10).

Studies have demonstrated that SMAD7 plays a role in diabetes and β-cell function. SMAD7, an intracellular protein, has been shown to interfere with binding of SMAD2/SMAD3 to the TGF-β1 R1 preventing phosphorylation and activation of these proteins, leading to inhibition of TGF-β1 mediated-signaling. Expression of SMAD7 in pancreatic β-cells has been shown to disrupt TGF-β signaling and induce reversible diabetes mellitus (Smart, N. G. et al. "Conditional expression of Smad7 in pancreatic beta cells disrupts TGF-beta signaling and induces reversible diabetes mellitus," *PLoS Biol.*, 2006, 4, e39). Furthermore, results in NOD mice also implicate the Smad2 and TGF-β signaling pathway in activated dendritic cells in diabetogenesis, and there is evidence from human genome-wide association studies supporting a role for Smad7 in human type 1 diabetes (Rook, S. M. et al. "Smad2: A candidate gene for the murine autoimmune diabetes locus Idd21.1," *J. Clin. Endocrinol. Metab.*, 2011, 96, E2072-E2077). Since TGF-β1 has been shown to contribute to the suppression of cytokine production, the inhibition of T cell response, and the induction of regulatory T cells (Treg) (Kawamoto, K. et al. "Transforming growth factor beta 1 (TGF-β1) and rapamycin synergize to effectively suppress human T cell responses via upregulation of FoxP3+ Tregs," *Transpl. Immunol.*, 2010, 23, 28-33), SMAD7 modulation could also be beneficial in islet transplantation by supporting graft function, limiting toxicity, and preventing immune rejection.

Thus, there is an unmet need for new therapies in diabetes and pancreatic islet transplantation.

SUMMARY

The disclosed methods are based, in part, upon the discovery of specific inhibitors of SMAD7 expression or function, e.g., antisense oligonucleotides against SMAD7, that inhibit SMAD7 and therefore restore TGF-β signaling. Exemplary antisense oligonucleotides against SMAD7 include, for example, SEQ ID No:5 or SEQ ID No: 6, which may be used in a pharmaceutical composition. The disclosed SMAD7 inhibitors can be used to treat and/or prevent diabetes, e.g., Type 1 diabetes, Type 2 diabetes, and gestational diabetes. The antisense oligonucleotides against SMAD7 can also be used to promote pancreatic islet cell survival after transplantation.

The foregoing aspects and embodiments of the invention may be more fully understood by reference to the following figures, detailed description and claims. As used herein, "including" means without limitation, and examples cited are non-limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 (A) provides the nucleic acid sequence of SMAD7 (SEQ ID NO: 1) and (B) provides the amino acid sequence of SMAD7 (SEQ ID NO: 2).

DETAILED DESCRIPTION

Figure 2A:
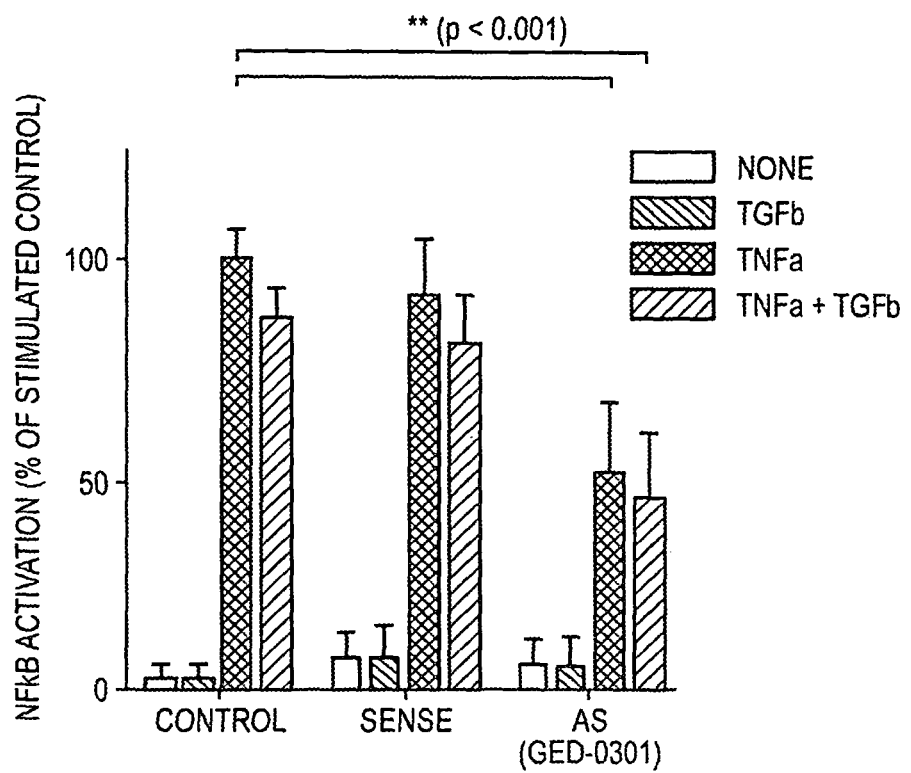
FIG. 2 (A) is a graph showing the effects of TGFβ and GED-0301 (a SMAD7 antisense oligonucleotide, SEQ ID NO: 6) on NF-κB activation in HEK-Blue TNF-α sensor cells and (B) is a graph showing the effect of TGFβ and GED-0301 on NF-κB activation in HEK-Blue CD40L sensor cells challenged by TNF-α and CD40L, respectively.

The present disclosure is generally directed to antisense oligonucleotides against SMAD7 and uses thereof in treating and/or preventing diabetes and/or in promoting pancreatic islet cell survival after transplantation.

Anti-SMAD7 Therapy

The disclosed methods relate to the use of a specific SMAD7 inhibitor selected from the group consisting of small binding molecules, e.g., natural and synthetic compounds, antibodies, aptamers, intramers, RNAi (double stranded RNA, siRNA) and anti-SMAD7 antisense molecules for treating and/or preventing diabetes and/or in promoting pancreatic islet cell survival after transplantation. SMAD7 inhibitors may also comprise truncated and/or mutated SMAD7 molecules which interfere with the SMAD7 and which, thereby, inhibit SMAD7 function.

For example, anti-SMAD7 therapy includes targeted therapies against SMAD7 (e.g., anti-SMAD7 antisense therapies, i.e., antisense oligonucleotide against SMAD7, and antibodies against SMAD7). Antisense oligonucleotides are short synthetic oligonucleotide sequences complementary to the messenger RNA (mRNA), which encodes for the target protein (e.g., SMAD7). Antisense oligonucleotide sequences hybridize to the mRNA producing a double-strand hybrid that can lead to the activation of ubiquitary catalytic enzymes, such as RNase H, which degrades DNA/RNA hybrid strands thus preventing protein translation.

In certain embodiments, an anti-SMAD7 antisense oligonucleotide may target site 403, 233, 294, 295, 296, 298, 299, and/or 533 (i.e., nucleotides 403, 233, 294, 295, 296, 298, 299, and 533, respectively) of the human SMAD7 mRNA (e.g., of SEQ ID NO: 1) (see FIG. 1). In an exemplary embodiment, the anti-SMAD7 antisense oligonucleotide targets nucleic acids 403-423 of human SMAD7 mRNA.

In certain embodiments, an antisense oligonucleotide may be derived from the following anti-SMAD7 antisense oligonucleotide 5'-GTCGCCCCTTCTCCCCGCAGC-3' (SEQ ID NO: 3).

It is contemplated herein that an antisense oligonucleotide targeting SMAD7 may comprise a mixed-backbone wherein the cytosine residues in a CpG pair are replaced by 5'-methylcytosine (abbreviated as Me-dC). Methylphosphonate linkages may also be placed at the 5' and/or 3' ends of an antisense oligonucleotide (abbreviated as MeP). The phosphonate backbone of a contemplated anti-SMAD7 antisense oligonucleotide may optionally include 1, 2, 3, 4 or more phosphorothioate bonds (e.g., phosphorothioate bonds would replace phosphodiester bonds). In an embodiment, all phosphonate bonds may be phosphorothioate bonds.

Exemplary antisense oligonucleotide therapies that target SMAD7 include, but are not limited to:

5'-GTXYCCCCTTCTCCCXYCAG-3' (SEQ ID NO: 4), wherein X is a nucleotide comprising a nitrogenous base selected from the group consisting of cytosine and 5-methylcytosine or a 2'-O-methylcytosine nucleoside, and wherein Y is a nucleotide comprising a nitrogenous base selected from the group consisting of guanine and 5-methylguanine or a 2'-O-methylguanine nucleoside, provided that at least one of the nucleotides X or Y comprises a methylated nitrogenous base;

5'-GTXGCCCCTTCTCCCXGCAG-3' (SEQ ID NO: 5), wherein X is 5-methyl 2'-deoxycytidine 5'-monophosphate;

5'-GTXGCCCCTTCTCCCXGCAGC-3' (SEQ ID NO: 6), wherein X is 5-methyl 2'-deoxycytidine 5'-monophosphate;

5'-ZTXGCCCCTTCTCCCXGCAZ-3' (SEQ ID NO: 7), wherein X is 5-methyl 2'-deoxycytidine 5'-monophosphate and Z is 2'-deoxyguanosine methylphosphonate;

5'-ZTXGCCCCTTCTCCCXGCAZC-3' (SEQ ID NO: 8), wherein X is 5-methyl 2'-deoxycytidine 5'-monophosphate and Z is 2'-deoxyguanosine methylphosphonate.

In a particular embodiment, contemplated SMAD7 antisense may be a sequence comprising one of:

5'-GTXGCCCCTTCTCCCXGCAG-3' (SEQ ID NO: 9), wherein X is 5-methyl 2'-deoxycytidine 5'-monophosphorothioate;

5'-GTXGCCCCTTCTCCCXGCAGC-3' (SEQ ID NO: 10), wherein X is 5-methyl 2'-deoxycytidine 5'-monophosphorothioate;

5'-ZTXGCCCCTTCTCCCXGCAZ-3' (SEQ ID NO: 11), wherein X is 5-methyl 2'-deoxycytidine 5'-monophosphate and Z is 2'-deoxyguanosine methylthiophosphonate;

5'-ZTXGCCCCTTCTCCCXGCAZC-3' (SEQ ID NO: 12), wherein X is 5-methyl 2'-deoxycytidine 5'-monophosphate and Z is 2'-deoxyguanosine methylthiophosphonate.

For example, SEQ ID NOs. 9-12 include 1, 2, 3, 4 or more phosphorothioate bonds. In an embodiment, all O,Ophosphonate bonds of SEQ ID NOs. 9-12 are phosphorothioate bonds.

Methods of Treatment

Provided herein are methods of promoting organ and/or cell, for example, pancreatic islet cell, survival after transplantation, comprising administering to a patient in need thereof an effective amount of a specific inhibitor of SMAD7 expression or function, for example, an antisense oligonucleotide against SMAD7.

Also, provided herein are methods of treating and/or preventing diabetes, e.g., Type 1 diabetes and Type 2 diabetes, comprising administering to a patient in need thereof an effective amount of a specific inhibitor of SMAD7 expression or function, for example, an antisense oligonucleotide against SMAD7.

Diabetes includes a group of metabolic diseases characterized by high blood sugar or ketoacidosis, as well as chronic, general metabolic abnormalities arising from a prolonged high blood sugar status or a decrease in glucose tolerance. Diabetes includes both the Type 1 and Type 2 forms of the disease, gestational diabetes, and other-conditions of insulin deficiency.

It will be appreciated that the disclosed methods are also applicable to treating and preventing latent autoimmune diabetes (i.e., type 1.5 diabetes), metabolic imbalances, a pre-diabetic state, metabolic syndrome, a lipid or glucose related disorder, e.g., hyperlipidemia and/or hypercholesterolemia, and other related disorders.

Metabolic imbalances can include any disorder or disease state or condition that are associated with an elevated plasma glucose. A metabolic imbalance, for example, comprises diabetes mellitus, gestational diabetes, genetic defects of β-cell function, genetic defects in insulin action, diseases of the exocrine pancreas, endocrinopathies, drug or chemical-induced infections, other genetic syndromes associated with diabetes, a pre-diabetic state, and metabolic syndrome.

Metabolic syndrome is characterized by a group of metabolic risk factors in one person, as described by the American Heart Association (AHA). Metabolic syndrome is also known as metabolic syndrome X, syndrome X, insulin resistance syndrome, Reaven's syndrome, or CHAOS. The risk factors include, but are not limited to, abdominal obesity, atherogenic dyslipidemia, hypertension, insulin resistance or glucose intolerance, prothrombotic state (high fibrinogen or plasminogen activator inhibitor-1), and proinflammatory state (elevated C-reactive protein).

The terms "treat", "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease.

In certain embodiments, a subject's responsiveness to treatment with an anti-SMAD7 therapy can be interpreted with respect to a control sample (described below) obtained from the subject prior to treatment. A subject may be identified as responding to treatment with an anti-SMAD7 therapy if there is a reduction in SMAD7 expression; if there is an increase in the total pancreatic insulin content; if β-cell function is maintained and/or restored (for example, as assessed via standard methods such as the intravenous glucose tolerance test, IVGTT); and/or if normoglycemic, i.e., normal glucose content of the blood, is maintained and/or restored. In other embodiments, a subject which has received an islet graft, e.g., an allogenic islet graft, may be identified as responding to treatment with anti-SMAD7 therapy if there is prevention of rejection and/or prolonged survival of the islets.

A test sample may be obtained from the patient, for example, at week 1, week 2, week 4, week 8, week 10 or later after initiation of therapy to determine sensitivity to treatment. In some embodiments, the test sample may be obtained, for example, one week, two weeks, three weeks, four weeks, five weeks, six weeks, seven weeks, eight weeks, nine weeks, ten weeks, eleven weeks, twelve weeks, five months, six months, and/or one year or longer after the initiation of therapy to monitor sensitivity to treatment.

A control sample may include a sample (e.g., a blood or tissue sample) obtained from the subject prior to treatment with an anti-SMAD7 therapy. The control sample provides a baseline for monitoring a subject's progress to treatment. A control sample may be obtained from the subject on the day the anti-SMAD7 therapy is first administered (e.g., Day 1 of a treatment regimen). In other embodiments, a control sample may be obtained from a subject one day prior to the start of an anti-SMAD7 therapy (e.g., Day 0 of a treatment regimen). Alternatively, a control sample may be obtained from a subject 2, 3, 4, 5, 6, 7 or more days prior to the start of an anti-SMAD7 therapy. For example, the upregulation or down regulation of certain cell samples may be measured prior to treatment (e.g., a control sample), during treatment, and/or after treatment to monitor a subject's response to therapy, e.g., an anti-SMAD7 therapy.

A control sample may include, for example, a sample to monitor the glucose level of a subject, wherein the sample was obtained from the subject prior to treatment with an anti-SMAD7 therapy.

In some embodiments, a control level may be established for a subject based on long-term monitoring of certain cell populations in the subject. In such instances, it is contemplated that a subject may undergo multiple rounds of treatment with an anti-SMAD7 therapy. The amount of a certain cell population detected following multiple rounds of treatment may be compared to a prior control level for the subject to determine whether the subject has responded to therapy and/or is likely to respond to further treatment with an anti-SMAD7 therapy. In other embodiments, a control or baseline level for a subject may be established based on an average measurement of a certain cell population determined from multiple baseline samples obtained over time (e.g., obtained over the course of weeks, months, or years). Accordingly, any test or assay conducted as disclosed herein may be compared with a previous or established control level and it may not be necessary to obtain a new control sample from the subject for comparison, e.g., if the subject is receiving more than one round of treatment with an anti-SMAD7 therapy.

Administration and Formulation

In some embodiments, contemplated herein are pharmaceutical compositions comprising a contemplated antisense oligonucleotide against SMAD7 and a pharmaceutically acceptable carrier. For example, the pharmaceutical composition may be administered subcutaneously. Alternatively, the pharmaceutical composition may be administered orally.

As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

In one embodiment, a contemplated antisense oligonucleotide against SMAD7 and any pharmaceutical composition thereof may be administered by one or several routes, including orally, topically, parenterally, e.g., subcutaneous injection, by inhalation spray or rectally. The term parenteral as used herein includes subcutaneous injections, intrapancreatic administration, intravenous, intramuscular, intraperitoneal, intrasternal injection or infusion techniques. For example, the antisense oligonucleotide against SMAD7 may be administered subcutaneously to a subject. In another example, the antisense oligonucleotide against SMAD7 may be administered orally to a subject.

Pharmaceutical compositions containing an antisense oligonucleotide against SMAD7, such as those disclosed herein, can be presented in a dosage unit form and can be prepared by any suitable method. A pharmaceutical composition should be formulated to be compatible with its intended route of administration. Useful formulations can be prepared by methods well known in the pharmaceutical art. For example, see *Remington's Pharmaceutical Sciences,* 18th ed. (Mack Publishing Company, 1990).

Pharmaceutical formulations preferably are sterile: Sterilization can be accomplished, for example, by filtration through sterile filtration membranes. Where the composition is lyophilized, filter sterilization can be conducted prior to or following lyophilization and reconstitution.

In an exemplary embodiment, a pharmaceutical composition for subcutaneous administration of an antisense oligonucleotide against SMAD7 comprises an antisense oligonucleotide such as that represented by SEQ ID NO: 6, or a pharmaceutically acceptable salt thereof (such as a sodium salt), and a pharmaceutically acceptable carrier.

In another embodiment, a pharmaceutical tablet formulation for oral administration of an antisense oligonucleotide against SMAD7 comprises an intragranular phase, wherein the intra-granular phase includes an antisense oligonucleotide such as that represented by SEQ ID NO: 6, or a pharmaceutically acceptable salt thereof (such as a sodium salt), and a pharmaceutically acceptable filler, and which may also include an extra-granular phase, that may include a pharmaceutically acceptable excipient such as a disintegrant. For example, a pharmaceutically acceptable tablet for oral use may comprise an intra-granular phase, comprising about 5 to about 10% by weight antisense oligonucleotide represented by SEQ ID NO 6 or a pharmaceutically acceptable salt thereof, about 40% by weight mannitol, about 8% by weight microcrystalline cellulose, about 5% by weight hydropropylmethyl cellulose, and about 2% by weight sodium starch glycolate; an extra-granular phase comprising about 17% by weight microcrystalline cellulose, about 2% by weight sodium starch glycolate, about 0.4% by weight magnesium stearate; and an enteric coating over the tablet, comprising about 13% by weight AcyrlEZE® (see, e.g., PCT Publication No: WO/2010/054826, which is hereby incorporated by reference in its entirety).

Exemplary formulations include dosage forms that include or consist essentially of about 35 mg to about 500 mg of an antisense oligonucleotide against SMAD7. For example, formulations that include about 35 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, or 250 mg of an antisense oligonucleotide against SMAD7 are contemplated herein. In one embodiment, a formulation may include about 40 mg, 80 mg, or 160 mg of an antisense oligonucleotide against SMAD7. The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue level. Alternatively, the initial dosage can be smaller than the optimum, and the dosage may be progressively increased during the course of treatment. Human dosage can be optimized, e.g., in a conventional Phase I dose escalation study designed to run from 40 mg to 160 mg. Dosing frequency can vary, depending on factors such as route of administration, dosage amount and the disease being treated. Exemplary dosing frequencies are once per day, once per week and once every two weeks. In some embodiments, dosing is once per day for 7 days. A preferred route of administration is subcutaneous.

In some embodiments, methods provided herein may further include administering at least one other agent that is directed to treatment of diseases and disorders disclosed herein. In one embodiment, contemplated other agents may be co-administered (e.g., sequentially or simultaneously).

Agents contemplated include immunosuppressive agents including glucocorticoids, cytostatics, antibodies, agents acting on immunophilins, interferons, opioids, TNF binding proteins, mycophenolate, and small biological agents. For example, contemplated immunosuppressive agents include, but are not limited to: tacrolimus, cyclosporine, pimecrolimus, sirolimus, everolimus, mycophenolic acid, fingolimod, dexamethasone, fludarabine, cyclophosphamide, methotrexate, azathioprine, leflunomide, teriflunomide, anakinra, anti-thymocyte globulin, anti-lymphocyte globulin, muromonab-CD3, afutuzumab, rituximab, teplizumab, efalizumab, daclizumab, basiliximab, adalimumab, infliximab, and etanercept.

Agents contemplated include drug therapies for regulating blood sugar levels including oral therapies with hypoglycemic agents and/or oral anti-diabetic agents, injectable therapies, and the like. Non-drug therapies for regulating blood sugar level include, but are not limited to, diatetic and/or exercise control measures.

Oral drug therapies for regulating blood sugar levels include hypoglycemic agents that may include, but are not limited to: Acarbose, Acetohexamide, Chlorpropamide, Darglitazone Sodium, Glimepiride, Glipizide, Glyburide, Repaglinide, Troglitazone, Tolazamide, and Tolbutamide.

Oral drug therapies for regulating blood sugar levels include antidiabetic agents that may include but are not limited to: Acarbose, Acetohexamide, Buformin, Butoxamine Hydrochloride, Camiglibose, Chlorpropamide, Ciglitazone, Englitazone Sodium, Etoformin Hydrochloride, Gliamilide, Glibornuride, Glicetanile Gliclazide Sodium, Gliflumide, Glipizide, Glucagon, Glyburide, Glyhexamide, Glymidine Sodium, Glyoctamide, Glyparamide, Insulin Isophane, Insulin Human Zinc, Extended Insulin, Insulin Lispro, Linogliride, Linogliride Fumarate, Metformin, Methyl Palmoxirate, Palmoxirate Sodium, Pioglitazone Hydrochloride, Pirogliride Tartrate, Proinsulin Human, Repaglinide, Seglitide Acetate, Tolazamide, Tolbutamide, Tolpyrramide, Troglitazone, and Zopolrestat.

Injectable therapies for regulating blood sugar levels may include, but are not limited to fast-acting insulin, long-acting insulin, and related insulin. Fast-acting insulin includes regular insulin, Prompt Insulin Zinc Suspension, and Semilente® insulin, Humalog® Injection, Humulin® R, Iletin II, Novolin R, Purified Pork Regular Insulin, and Velosulin BR Human Insulin. Long-acting insulin includes Protamine Zinc Insulin Suspension, Extended Insulin Zinc Suspension, Ultralente® Insulin, and Humulin® U. Other insulin includes Isophane Insulin Suspension, NPH insulin, isophane insulin; Insulin Zinc Suspension Lente® Insulin, Human Insulin Isophane Suspension/Human Insulin Injection, Humulin® 50/50, Humulin® 70/30, and Novolin® 70/30.

EXAMPLES

The invention is further illustrated by the following examples. The examples are provided for illustrative purposes only, and are not to be construed as limiting the scope or content of the invention in any way.

Example 1

Effect of SMAD7 Antisense on NF-κB Activation

HEK-Blue™ (InvivoGen) TNF-α/IL-1β sensor cells are designed to detect bioactive TNF-α and IL-1β by monitoring the activation of the NF-κB pathway. These cells were generated by stable transfection of human embryonic kidney HEK293 cells with a SEAP reporter gene under the control of the IFN-β minimal promoter fused to five NF-κB and five AP-1 binding sites. HEK-Blue™ (InvivoGen) CD40L sensor cells are used to measure the bioactivity of CD154 (CD40L) through the secretion of embryonic alkaline phosphatase (SEAP) upon NF-κB activation following CD40 stimulation. These cells were generated by stable transfection of HEK293 cells with the human CD40 gene and an NF-κB-inducible SEAP construct. Therefore, HEK-Blue™ cells measure the bioactivity of TNFα/CD40L through the secretion of embryonic alkaline phosphatase (SEAP) upon NF-κB activation following TNFR/CD40 stimulation. Tumor necrosis factor alpha (TNF-α) is a known cytokine involved in systemic inflammation and the regulation of immune cells. CD40L is a co-stimulatory protein involved in T-cell activation and the development of effective immune responses, and is thought to be involved in the development of autoimmune diseases including T1DM (Margolles-Clark, E. et al. "Small molecule costimulatory blockade: organic dye inhibitors of the CD40-CD154 interaction," *J. Mol. Med.*, 2009, 87, 1133-1143).

HEK Blue TNFα and CD40L sensor cells (Invivogen) (50,000/well) were incubated with GED-0301 antisense (AS) or control sense (S) oligonucleotide (OGN; 4 μg/mL) for 6 h in the presence of lipofectamine (LPF) then media for 18 h followed by challenge by TNFα (1 ng/mL) or CD40L (25 ng/mL) in the presence or absence of TGF-β (200 ng/mL; 24 h, DMEM P/S 2% serum). GED-0301 is an SMAD7 antisense oligonucleotide (GTXGCCCCTTCTC-CCXGCAGC, wherein X is 5-methyl-2'-deoxycytidine 5' monophosphate (5-Me-dC) (SEQ ID NO: 6)). Secretion of SEAP induced by TNFα or CD40L in these cells was quantified using QUANTI-Blue™, a colorimetric enzyme assay provided by the manufacturer and specifically developed for this purpose with a medium that changes to a purple-blue color in the presence of SEAP, which can be quantified by reading OD at 625-655 nm. Data are the average of three independent experiments with quadruplicates per plate using values normalized to the stimulated response (TNFα or CD40L alone) in untreated control cells.

Figure 2B:
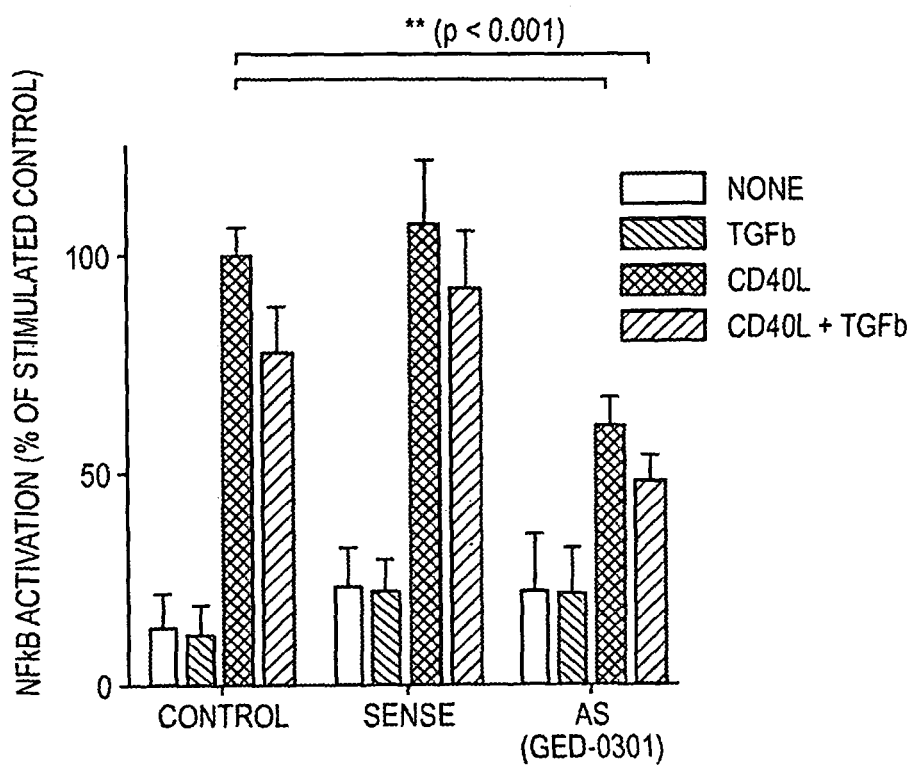

The effects of TGF-β and GED-0301 on NF-κB activation in HEK-Blue cells by TNFα and CD40L, respectively are shown in FIGS. 2A and 2B. Results show that both TNFα and CD40L produced considerable NF-κB activation (as measured by SEAP expression) and these were both suppressed by TGF-β. This suppression was considerably enhanced further by treatment with the SMAD7 antisense oligonucleotide GED-0301 indicating that this treatment can enhance and/or restore the effects of TGF-β. In cell culture systems, TGF-β can either promote or inhibit NF-κB activation depending on the cell type used (Hong, S. et al. "Smad7 sensitizes tumor necrosis factor induced apoptosis through the inhibition of antiapoptotic gene expression by suppressing activation of the nuclear factor-kappaB pathway," *Cancer Res.*, 2007, 67, 9577-9583 and references therein). TGF-β was a negative regulator of NF-κB in B cells and in human intestinal lamina propria mononuclear cells (LPMC). The results for transfected HEK cells are similar to those observed for LPMC, where it has been shown that TGF-β1 negatively regulates NF-κB activation in normal LPMC (as pretreatment with TGF-β1 suppressed TNF-α-induced NF-κB activation), and that treatment of IBD LPMC with a specific Smad7 antisense resulted in inhibition of NF-κB activation (Monteleone, G. et al. "A failure of transforming growth factor-β1 negative regulation maintains sustained NF-κB activation in gut inflammation," *J. Biol. Chem.*, 2004, 279, 3925-3932).

To confirm that GED-0301 can penetrate the assayed cells, HEK Blue sensor cells (50,000/well) were incubated with fluorescein-labeled GED-0301 AS OGN for 48 h in the presence or absence of lipofectamine (LPF, Invitrogen) and then analyzed for cellular uptake. Microscope imaging confirmed that the HEK Blue sensor cells which were incubated with fluorescein-labeled GED-0301 in the presence of lipofectamine displayed uptake of the fluorescein-labeled GED-0301 better than cells not treated with lipofectamine.

Example 2

Distribution Study of SMAD7 Antisense in Mice

Figure 3A:
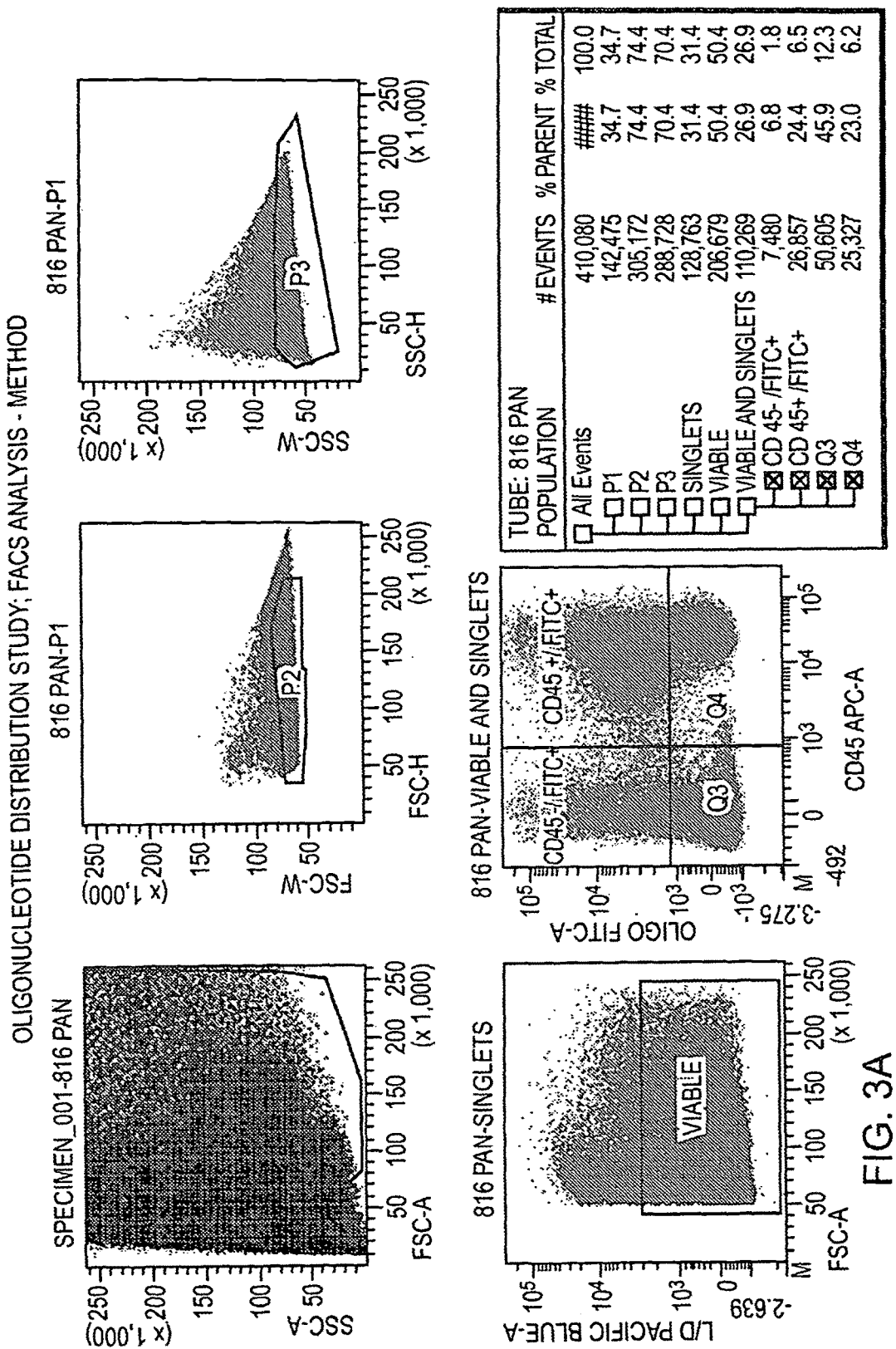
FIG. 3 (A) is a panel illustrating the gating methodology used in analysis of flow cytometry results for the organ-specific uptake of fluorescein-labeled GED-0301 following administration by various routes in mice and FIG. 3 (B) shows corresponding percent uptakes (FITC+) in viable cells in the indicated organ tissues.
Figure 3B:
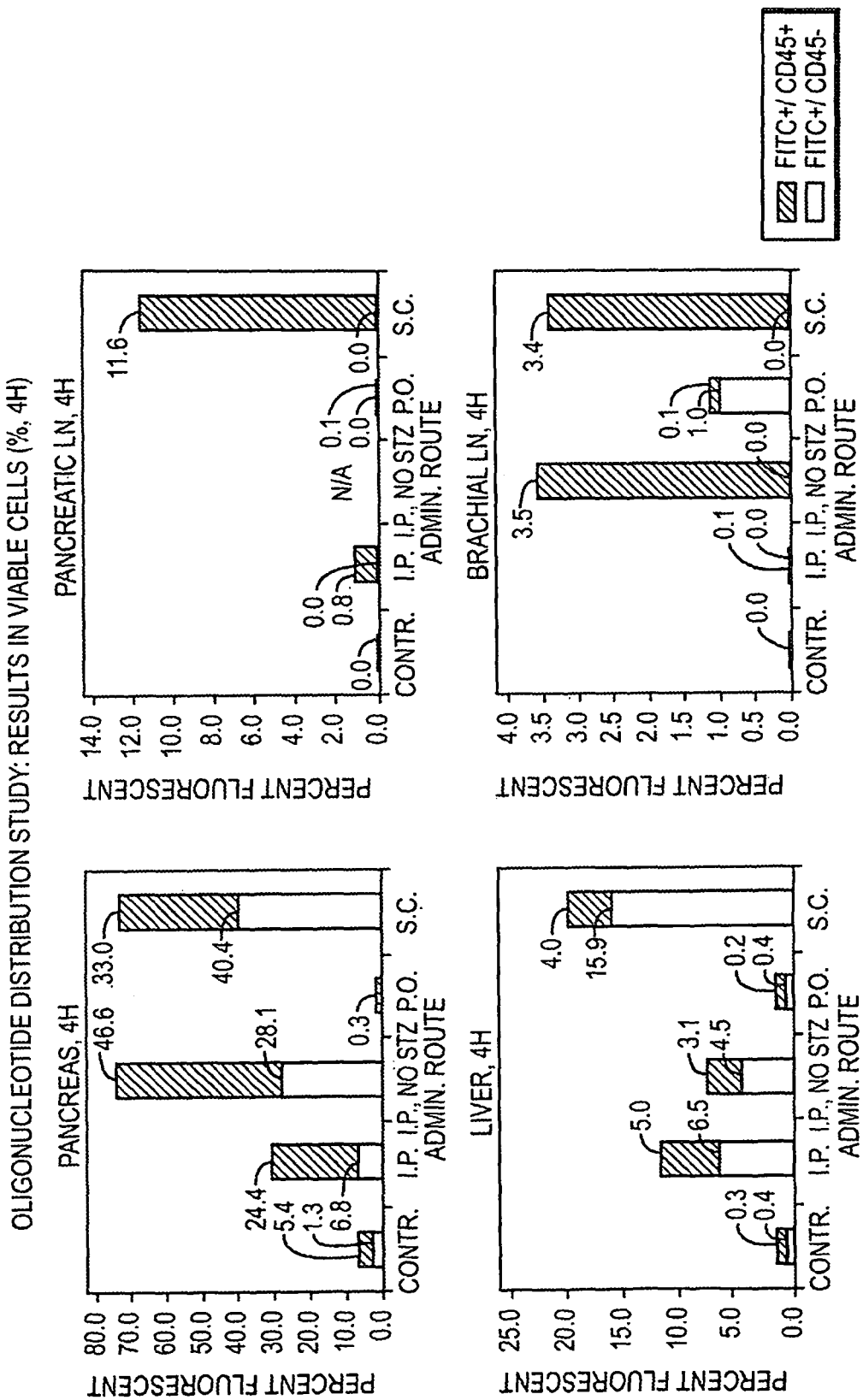
Figure 3B:
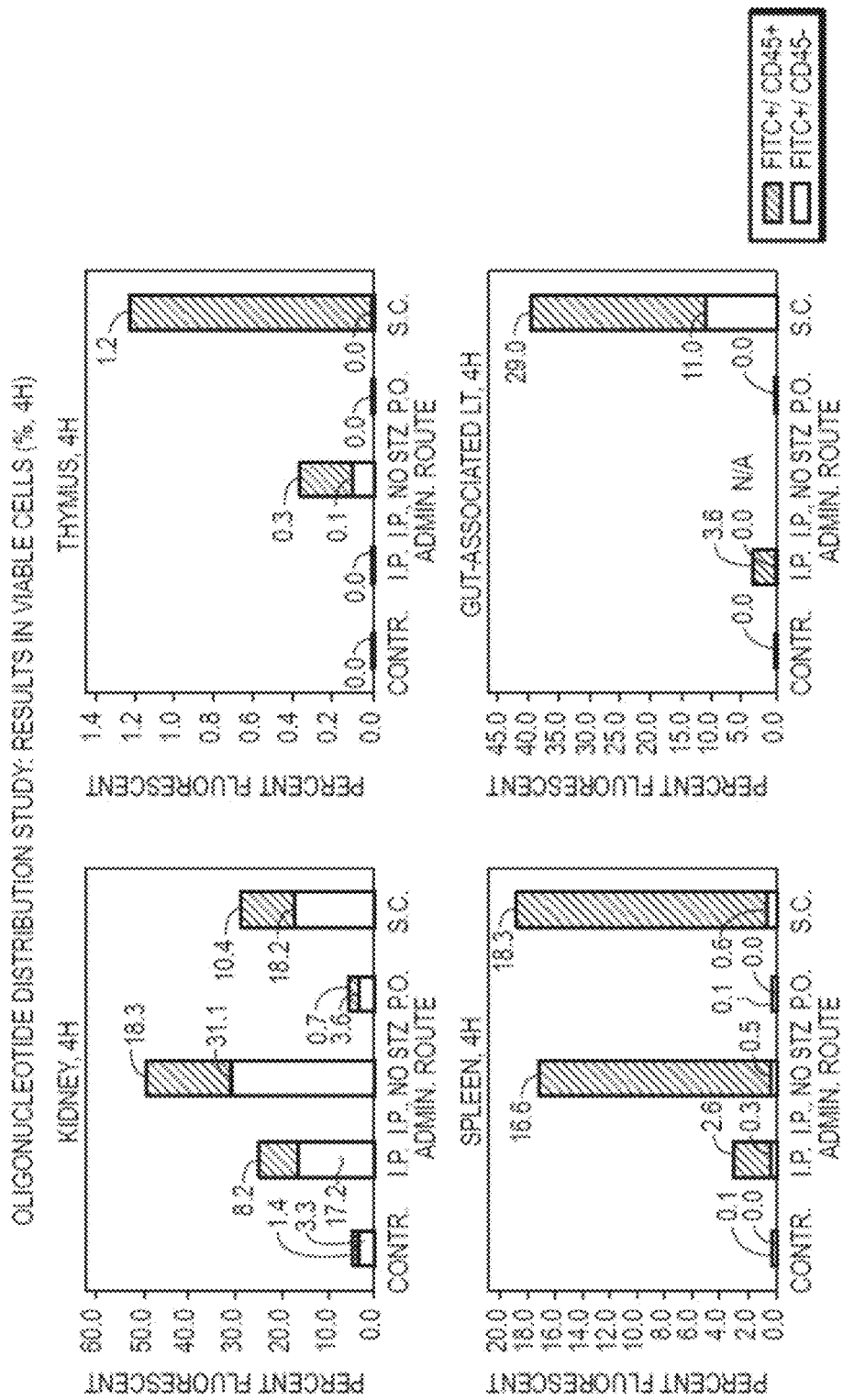

Regular B6 mice (6 wk, males; Jackson Lab.) with multiple low-dose streptozotocin-induced diabetes (STZ, a β-cell specific toxin; 40 mg/kg i.p. for 5 consecutive days) were administered fluorescein-labeled GED-0301 antisense oligonucleotides (TriLink) by three different routes: oral (p.o.), intraperitoneal (i.p.), and subcutaneous (s.c.) (125 µg/mouse=5 mg/kg; p.o. by oral gavage using 500 µL bicarbonate solution, pH 9.5 to protect from gastric degradation). At two different time-points (4 h and 24 h), organs were collected and processed from two different animals (one for microscopy, one for flow cytometry). The following organs were collected: pancreas, liver, kidney, spleen, thymus, intestine, brain, blood, pancreatic lymph nodes, brachial lymph node, gut-associated lymphoid tissue. For flow cytometry analysis, organs were digested using collagenase D (Roche), passed through a cell strainer (70 µm; BD Falcon), re-suspended in HBSS, and stained for live cells (LIVE/DEAD® fixable violet dead cell stain kit; Invitrogen) and for leukocytes (anti-mouse CD45 APC; eBioscience). They were then analyzed for fluorescein content m viable cells by using a BD LSR II Flow Cytometer (BD Biosciences, San Jose, Calif.) and the software FlowJo version 7.2.2 (Ashland, Oreg.). FIG. 3A shows an example to illustrate the gating methodology used to analyze the flow cytometry results. FIG. 3B includes illustrative flow cytometry results obtained for the corresponding percent uptakes in viable cells in specific organs, and they demonstrate significant antisense oligonucleotide uptake (percent FITC+) by the pancreas, pancreatic lymph nodes, and other organs (both in leukocytes, CD45+/FITC+, and in other cells, CD45−/FITC+), especially following s.c. administration. Some organs such as the brain showed no significant uptake. These results confirm that GED-0301 can be delivered to specific organs using clinically acceptable administration routes including subcutaneous administration.

Figure 4:
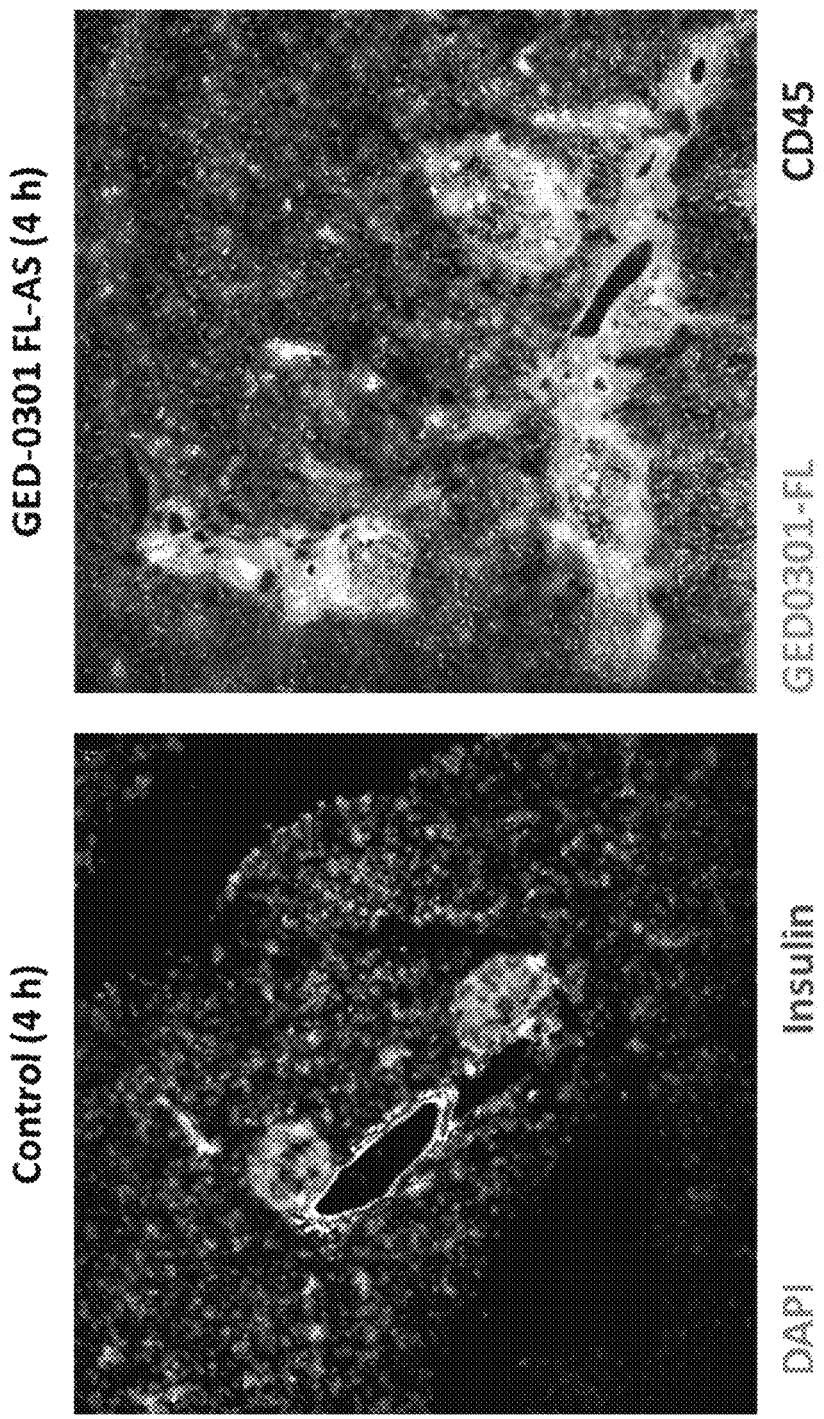
FIG. 4 is a multichannel high resolution microscopic image depicting sections of pancreas from a control mouse and a mouse administered fluorescein-labeled GED-0301 subcutaneously (4 hours after administration). Color legend: green—fluorescent GED-0301, grey—DAPI (a marker of cell nucleus), red—insulin (indicating insulin-producing (β-cells), and blue—CD45 (indicating CD45 or leukocyte common antigen, LCA, a marker of white blood cells, the elements of the circulating blood system that comprise the cells of immunity and inflammation).

Multichannel high resolution microscopic images (FIG. 4) confirmed the distribution of GED-0301 into the pancreas of mouse following subcutaneous administration of the fluorescently labeled antisense oligonucleotide in agreement with the flow cytometry results (FIG. 3B). Color legend: green—fluorescent GED0301, grey—DAPI (a marker of cell nucleus), red—insulin (indicating insulin-producing β-cells), and blue—CD45 (indicating CD45 or leukocyte common antigen, LCA, a marker of white blood cells, the elements of the circulating blood system that comprise the cells of immunity and inflammation)

Example 3

In Vivo Studies with SMAD7 Antisense

Further in vivo studies can be used to establish the effect of the treatment in animal models.
Hyperglycemia Reversal Study of SMAD7 Antisense in NOD Mice
Non-obese diabetic (NOD) mice, e.g., NOD mice were used for an intervention-type diabetes prevention trial with treatment started only upon onset of hyperglycemia. NOD mice are a commonly used animal model of type 1 diabetes (Roep, B. O. et al. Satisfaction (not) guaranteed: re-evaluating the use of animal models of type 1 diabetes. *Nat. Rev. Immunol.*, 2004, 4, 989-997), and they have been used to evaluate a large number of possible treatments (Shoda, L. K. et al. "A comprehensive review of interventions in the NOD mouse and implications for translation," *Immunity*, 2005, 23, 115-126). Eight week old prediabetic female animals were procured (Taconic), and starting from week 10 (following acclimatization), glycosuria was monitored twice a week. In animals that turned positive, blood glucose levels (glycemia) were monitored three times a week. Animals with elevated glucose levels (nonfasting glycemia>200 mg/dL) on two consecutive days, received one sustained-release insulin pellet implant (LinBit, LinShin Canada, Inc.) to avoid severe hyperglycemia and exhaustion/over-work of the remaining β-cells; and they were started on treatment. Treatments were administered s.c., since this route is clinically relevant and the distribution studies described above indicated it to be effective in targeting the pancreas, the pancreatic LN, and other organs of possible interest. Animals were assigned to one of three treatment arms following a predefined rotating pattern in the order of their hyperglycemia development. Treatment (GED-0301=Smad7 AS OGN; 125 µg/mouse) and corresponding controls (S OGN and saline only) were administered daily. Animals were monitored twice weekly and assessed for their ability to maintain normoglycemia. Following the disappearance of the effects of the implanted insulin pellets (approximately 25 days), animals with three consecutive glucose readings of >250 mg/dL were considered as diabetic and sacrificed with representative organs (pancreas, PLN) collected. In animals that did not become diabetic, daily treatment was stopped after 10 weeks, and they were monitored for an additional 12 weeks (up to a total of 150 days) to establish whether there is a lasting effect. At the end, all animals were sacrificed and representative organs (pancreas, PLN, and others) collected.

Figure 5A:
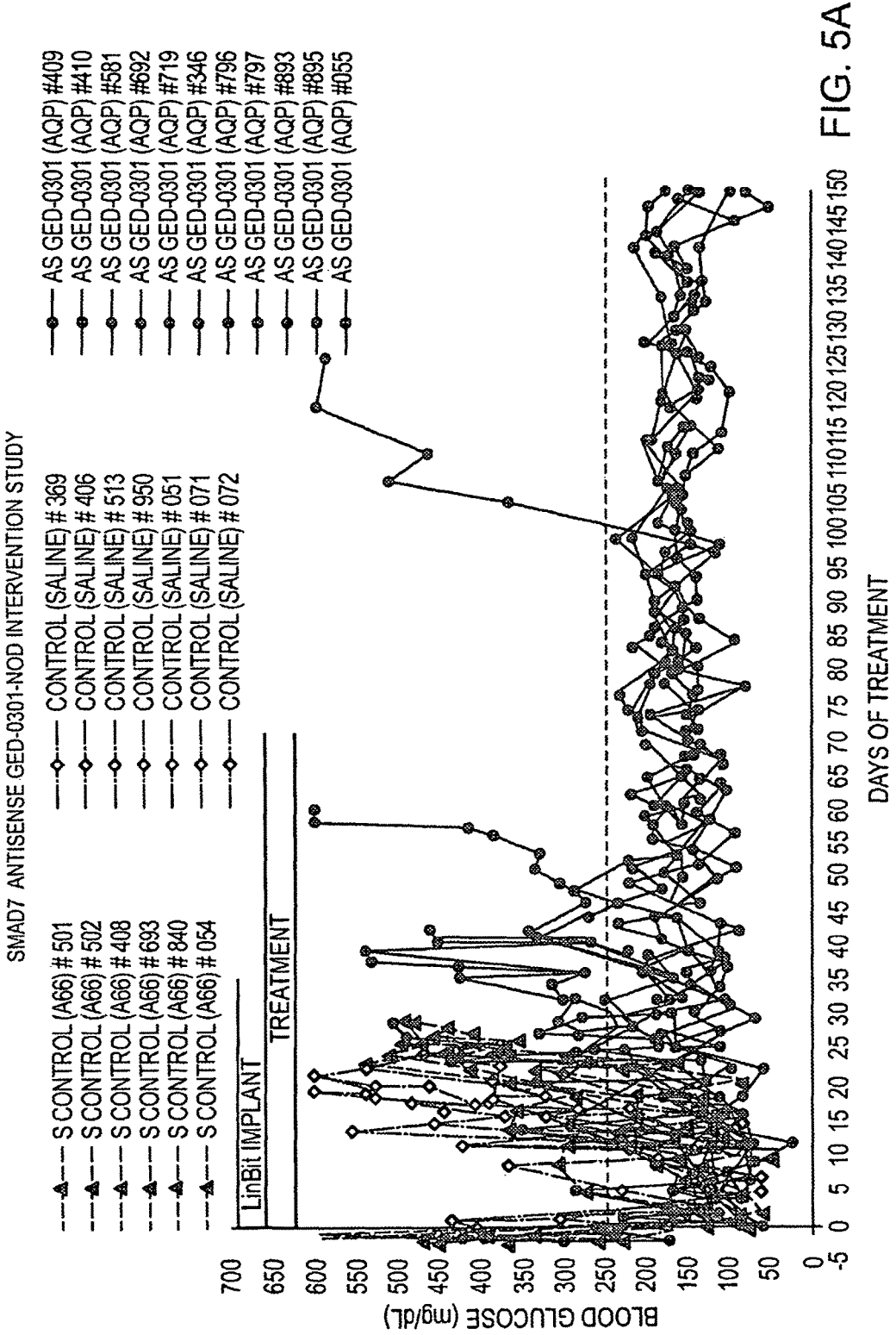
FIG. 5(A) is a graph depicting blood glucose levels in NOD mice treated with the SMAD7 antisense oligonucleotide GED-0301 (AS GED-0301), the corresponding sense control (S control), and saline (Control) (125 μg/animal, subcutaneous (s.c.), daily) following onset of hyperglycemia and FIG. 5 (B) is a corresponding Kaplan-Meier survival curve showing the percent of animals remaining diabetes-free as a function of time.
Figure 5B:
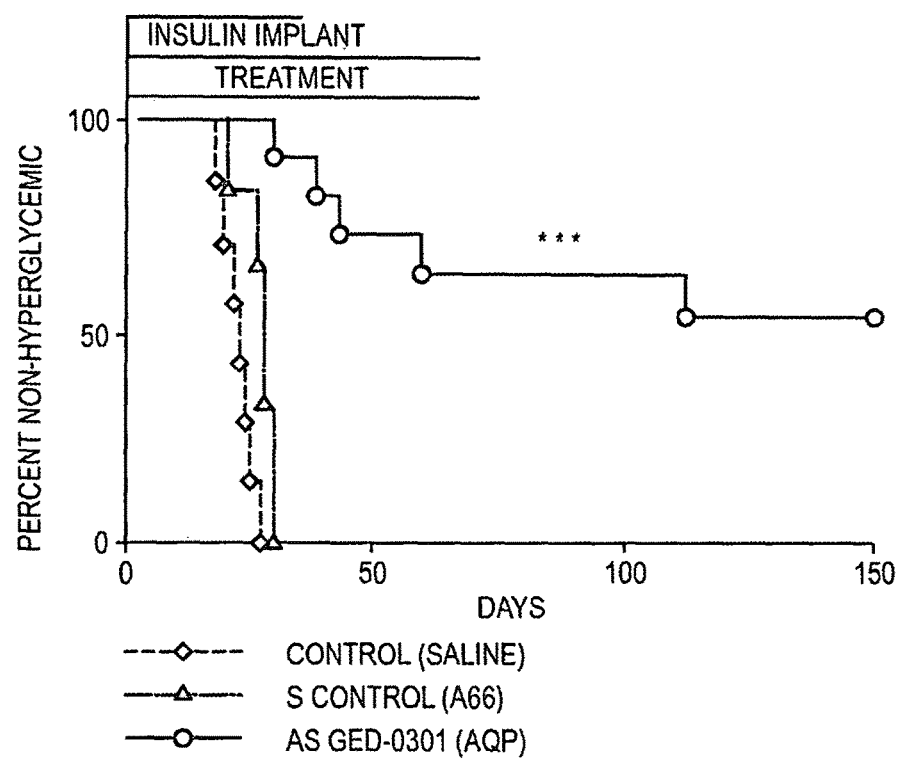

Results from the study are shown in FIG. 5 with blood glucose levels in FIG. 5A and a corresponding Kaplan-Meier survival curve showing the percent of animals remaining diabetes-free as a function of time in FIG. 5B. Treatment was initiated after the onset of hyperglycemia when β-cell damage had already occurred. Accordingly, severe hyperglycemia can develop very quickly. All animals treated with saline or sense oligonucleotide control developed diabetes (n=7 and 6, respectively), as indicated by their hyperglycemia (blood glucose>250 mg/dL) following the exhaustion of the LinBit implant with sustained release insulin by day 20-25. For the animals treated with the active GED-0301 antisense oligonucleotide, 6 out of the 11 treated did not develop hyperglycemia and they remained diabetes-free up to the end of the study (day 150), long after the treatment had been stopped (day 70).

Figure 6:
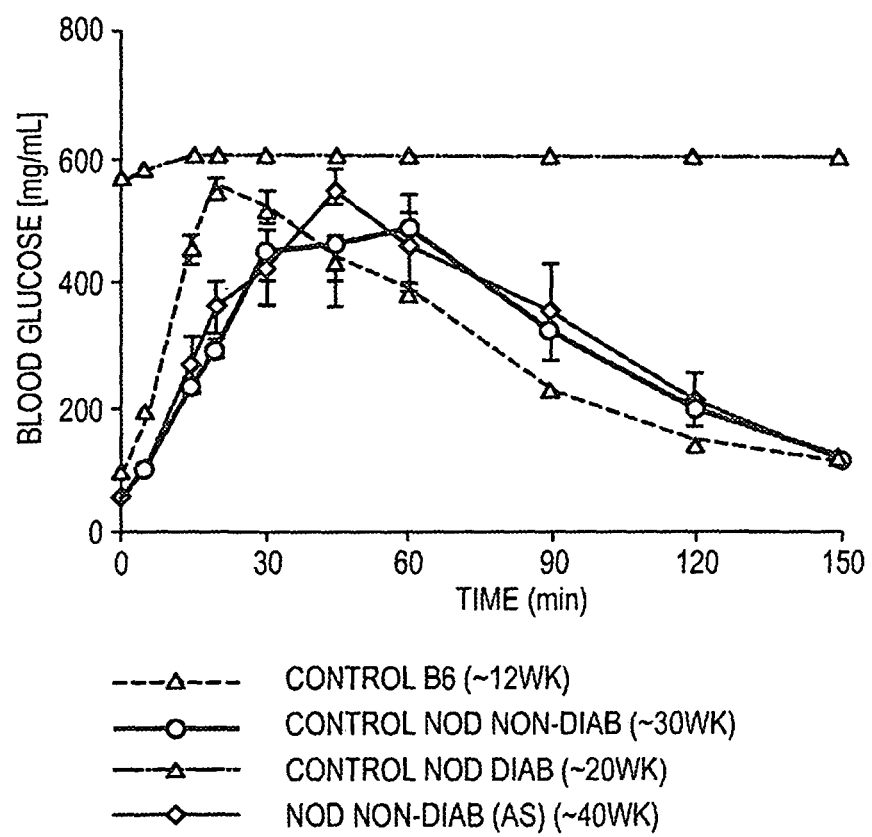
FIG. 6 is a graph comparing the results of an oral glucose tolerance test conducted in GED-0301-treated NOD mice that did not become diabetic by the end of the study (day 150) and control mice.

To verify the glucose response of non-diabetic animals at the end of the study (day 150), an oral glucose tolerance test (OGTT) was performed in several GED-0301-treated as well as control mice. A glucose dose of 150 mg was administered by oral gavage to mice fasted for 16 h and blood samples were collected at predefined time intervals for up to 150 minutes. Results shown in FIG. 6 confirm that the glucose response, and hence insulin-secreting ability, was comparable to that of healthy animals. Blood glucose levels returned to normal within 150 minutes of the oral challenge in all animals.

Figure 7:
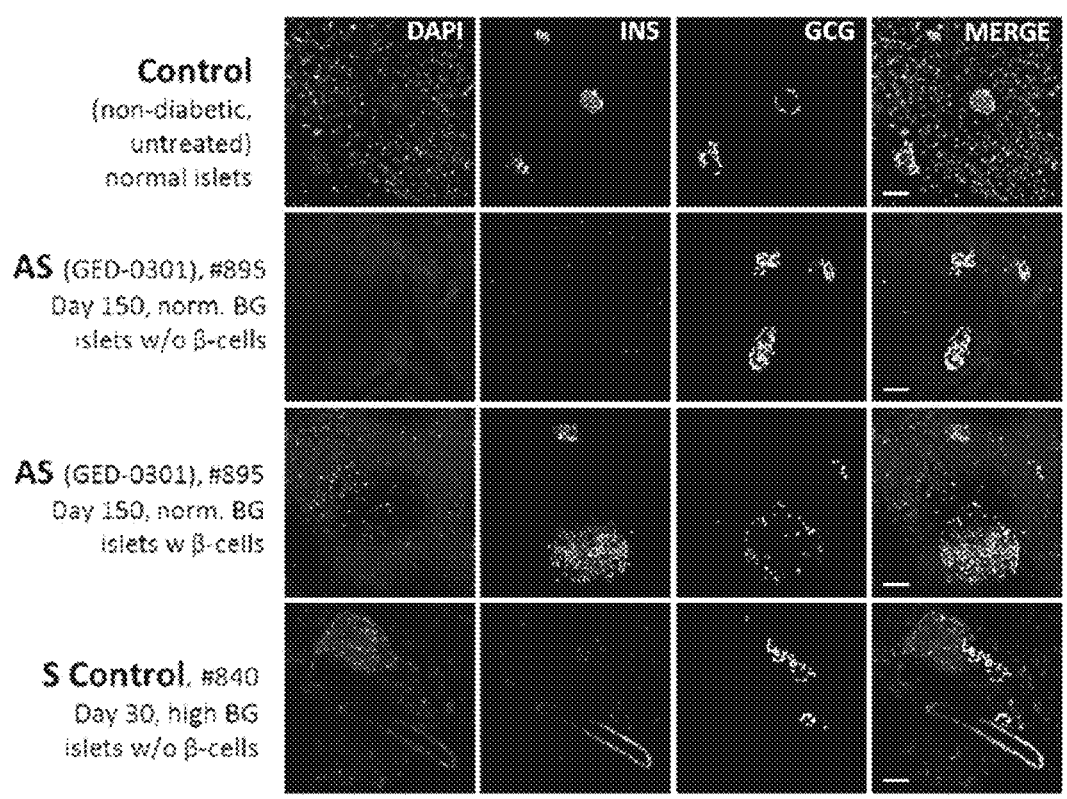
FIG. 7 shows multichannel high resolution Z-stacks of confocal microscopic images comparing representative islet-containing sections of pancreas from GED-0301-treated NOD mice that did not become diabetic by the end of the study (day 150) to those of corresponding controls. Color legend: blue—DAPI (a marker of cell nucleus), red—insulin (indicating insulin-producing β-cells), and green—glucagon (indicating glucagon-producing α-cells).

High-resolution confocal microscopic imaging of pancreas sections from GED-0301-treated NOD mice that did not become diabetic by the end of the study (day 150) was performed to confirm the presence of insulin-producing β-cells. FIG. 7 shows a series of multichannel Z-stack images of representative islet-containing sections of pancreas from GED-0301-treated mice and corresponding controls. Different colors (columns) are as follows: blue is DAPI (a marker of cell nucleus), red is insulin (indicating insulin-producing β-cells), and green is glucagon (indicating glucagon-producing α-cells). The scale bar indicates 100 µm. Whereas normal, non-diabetic control animals had normal islets containing both insulin- and glucagon-producing cells (top row), NOD mice that became diabetic during the study lost the insulin-producing β-cells from their islets (bottom row; from a sense oligonucleotide-treated mouse that did not revert to normoglycemia). GED-0301 antisense (AS) treated animals that did not become diabetic following treatment initiated at the onset of hyperglycemia had several islets that lost their insulin-producing cells (second row from top showing the presence of glucagon, but not insulin), but they also had islets with conserved insulin-producing cells (third row from top). Hence, GED-0301 treatment initiated at the onset of hyperglycemia seemed to be able to counter the effects of autoimmune attack in NOD mice and preserve insulin-producing β-cells in sufficient numbers to maintain normal blood glucose response and avoid the onset of hyperglycemia.

Study of SMAD7 Antisense in Islet Transplantation

Restoration of TGF-β signaling in the local microenvironment has shown promise in experimental allogeneic islet transplantation models, including in the presence of an underlying autoimmune disease. Treatment with GED-0301 can be done to establish the effect of an antisense targeting SMAD7 on the survival and/or tolerance to allogeneic islet grafts. Specifically, the effect of GED-0301 in preventing rejection and/or prolonging survival of islets in a model of allogeneic transplantation in rodents rendered diabetic by the administration of a beta cell-specific toxin (STZ) can be determined. Primary endpoints can include islet allograft survival, activation markers on T lymphocytes, dendritic cells, frequency and suppressive function of Treg and other suppressor cells as a correlation with Smad7 expression/modulation in the transplantation site.

Study of SMAD7 Antisense and Low-Grade Inflammation in Type 2 Diabetes

As low-grade systemic and local inflammation characterizes prediabetes and type 2 diabetes, the potential role of SMAD7 in the development of the low-grade inflammation within the pancreatic islet can be determined. Furthermore, the role of SMAD7 in islet vascular complications in diabetes can be studied.

Study of SMAD7 Antisense in Diabetic Nephropathy

In human diabetic nephropathy and other proteinuric glomerular diseases, Smad7 is strongly upregulated. This upregulation occurs primarily in podocytes, the glomerular cells responsible for the integrity of the glomerular filtration barrier and for the prevention of albuminuria, an independent predictor of cardiovascular outcome in the general population. Targeting of TGF-beta has been the topic of an intense translational effort (trial with pirfenidone). In these efforts, results have been unexpectedly negative for the cure of diabetic nephropathy and other chronic kidney diseases. Restoring a proper TGF-β signaling by Smad7 inhibition may be a promising and novel approach to treat these conditions. Established experimental models of diabetic nephropathy developed by the NIH Consortium on Diabetic Complications can be utilized to generate preliminary in vivo data on soft and hard renal outcome (albuminuria, glomerular filtration rate, glomerulosclerosis). Subsequent clinical studies can be developed in the Diabetic Nephropathy clinic at the Diabetes Research Institute.

Study of SMAD7 Antisense on Glucose Stimulated Insulin Secretion

Mice with pancreatic β-cells with Smad7 overexpression are characterized by impairment of insulin release and increased fasting glucose. Therefore, Smad7 inhibition could result in the improvement of pancreatic β-cell function. Glucose-stimulated insulin-release experiments in human islets genetically manipulated to express different level of SMAD7 can be performed. In further studies, human patients can be studied to determine the role of Smad7 inhibition in glucose intolerance in pre-diabetic subjects.

INCORPORATION BY REFERENCE

The entire disclosure of each of the patent documents and scientific articles cited herein is incorporated by reference for all purposes.

EQUIVALENTS

The invention can be embodied in other specific forms with departing from the essential characteristics thereof. The foregoing embodiments therefore are to be considered illustrative rather than limiting on the invention described herein. The scope of the invention is indicated by the appended claims rather than by the foregoing description, and all changes that come within the meaning and range of equivalency of the claims are intended to be embraced therein.

The invention claimed is:

1. A method of treating diabetes by preventing pancreatic islet β cell destruction, the method comprising administering to a patient in need thereof an effective amount of a SMAD7 antisense oligonucleotide comprising a sequence selected from the group consisting of the nucleotide sequences of SEQ ID NO: 3, SEQ ID NO: 6, SEQ ID NO: 8, SEQ ID NO: 10, and SEQ ID NO: 12, wherein the diabetes is selected from the group consisting of Type 1 diabetes, Type 2 diabetes, and gestational diabetes.

2. The method of claim 1, wherein the SMAD7 antisense oligonucleotide comprises the nucleotide sequence of SEQ ID NO: 6 or SEQ ID NO: 10.

3. The method of claim 1, wherein the SMAD7 antisense oligonucleotide is administered parenterally.

4. The method of claim 3, wherein the SMAD7 antisense oligonucleotide is administered subcutaneously.

5. The method of claim 1, wherein the SMAD7 antisense oligonucleotide comprises the nucleotide sequence of SEQ ID NO: 10.

6. The method of claim 5, wherein all internucleoside bonds of the SMAD7 antisense oligonucleotide comprising the nucleotide sequence of SEQ ID NO: 10 are phosphorothioate bonds.

7. The method of claim 1, wherein two or more of the internucleoside bonds of the SMAD7 antisense oligonucleotide comprising SEQ ID NO: 10 are phosphorothioate bonds.

8. A method of treating diabetes by preventing pancreatic islet β cell destruction, the method comprising administering to a patient in need thereof a pharmaceutical composition comprising:

an effective amount of a SMAD7 antisense oligonucleotide comprising a sequence selected from the group consisting of the nucleotide sequences of SEQ ID NO: 3, SEQ ID NO: 6, SEQ ID NO: 8, SEQ ID NO: 10, and SEQ ID NO: 12; and a pharmaceutically acceptable carrier, wherein the diabetes is selected from the group consisting of Type 1 diabetes, Type 2 diabetes, and gestational diabetes.

9. The method of claim 8, wherein the SMAD7 antisense oligonucleotide comprises the nucleotide sequence of SEQ ID NO: 6 or SEQ ID NO: 10.

10. The method of claim 8, wherein the SMAD7 antisense oligonucleotide comprises the nucleotide sequence of SEQ ID NO: 10.

11. The method of claim 10, wherein all internucleoside bonds of the SMAD7 antisense oligonucleotide comprising the nucleotide sequence of SEQ ID NO: 10 are phosphorothioate bonds.

12. The method of claim 8, wherein the pharmaceutical composition is administered parenterally.

13. The method of claim 12, wherein the pharmaceutical composition is administered subcutaneously.

14. The method of claim 8, wherein two or more of the internucleoside bonds of the SMAD7 antisense oligonucleotide comprising SEQ ID NO: 10 are phosphorothioate bonds.

15. A method of treating hyperglycemia by preventing pancreatic islet β cell destruction, the method comprising administering to a patient in need thereof an effective amount of a SMAD7 antisense oligonucleotide comprising a sequence selected from the group consisting of the nucleotide sequences of SEQ ID NO: 3, SEQ ID NO: 6, SEQ ID NO: 8, SEQ ID NO: 10, and SEQ ID NO: 12.

16. The method of claim 15, wherein the SMAD7 antisense oligonucleotide comprises the nucleotide sequence of SEQ ID NO: 10.

17. The method of claim 16, wherein all internucleoside bonds of the SMAD7 antisense oligonucleotide comprising the nucleotide sequence of SEQ ID NO: 10 are phosphorothioate bonds.

18. The method of claim 15, wherein the SMAD7 antisense oligonucleotide is administered parenterally.

19. The method of claim 18, wherein the SMAD7 antisense oligonucleotide is administered subcutaneously.

20. The method of claim 15, wherein two or more of the internucleoside bonds of the SMAD7 antisense oligonucleotide comprising SEQ ID NO: 10 are phosphorothioate bonds.

21. A method of treating hyperglycemia by preventing pancreatic islet β cell destruction, the method comprising administering to a patient in need thereof a pharmaceutical composition comprising:
   an effective amount of a SMAD7 antisense oligonucleotide comprising a sequence selected from the group consisting of the nucleotide sequences of SEQ ID NO: 3, SEQ ID NO: 6, SEQ ID NO: 8, SEQ ID NO: 10, and SEQ ID NO: 12; and
   a pharmaceutically acceptable carrier.

22. The method of claim 21, wherein the SMAD7 antisense oligonucleotide comprises the nucleotide sequence of SEQ ID NO: 10.

23. The method of claim 22, wherein all internucleoside bonds of the SMAD7 antisense oligonucleotide comprising the nucleotide sequence of SEQ ID NO: 10 are phosphorothioate bonds.

24. The method of claim 21, wherein the pharmaceutical composition is administered parenterally.

25. The method of claim 24, wherein the pharmaceutical composition is administered subcutaneously.

26. The method of claims 21, wherein two or more of the internucleoside bonds of the SMAD7 antisense oligonucleotide comprising SEQ ID NO: 10 are phosphorothioate bonds.

\* \* \* \* \*